United States Patent [19]
Reichert et al.

[11] Patent Number: 6,140,555
[45] Date of Patent: Oct. 31, 2000

[54] METHODS FOR MAIZE TRANSFORMATION COUPLED WITH ADVENTITIOUS REGENERATION UTILIZING NODAL SECTION EXPLANTS AND MATURE ZYGOTIC EMBRYOS

[75] Inventors: Nancy A. Reichert; Vanishree Rudraswamy, both of Starkville, Miss.

[73] Assignee: Mississippi State University, Mississippi State, Miss.

[21] Appl. No.: 09/092,180

[22] Filed: Jun. 5, 1998

Related U.S. Application Data

[60] Provisional application No. 60/048,678, Jun. 6, 1997.

[51] Int. Cl.$^7$ .............................. A01H 4/00; A01H 1/00; C12N 5/04; C12N 15/82; C12N 15/87
[52] U.S. Cl. .......................... 800/293; 800/278; 435/420; 435/424; 435/430; 435/431; 435/470
[58] Field of Search ................................... 800/293, 278; 435/420, 424, 430, 431, 470

[56] References Cited

U.S. PATENT DOCUMENTS

| | | | |
|---|---|---|---|
| 5,164,310 | 11/1992 | Smith et al. | 435/172.3 |
| 5,583,210 | 12/1996 | Neill et al. | 536/23.6 |
| 5,736,369 | 4/1998 | Bowen et al. | 435/172.3 |

OTHER PUBLICATIONS

Hartmann et al, Plant Science; Growth, Development, and Utilization of Cultivated Plants, Prentice–Hall, Inc., Englewood Cliffs, New Jersey, p. 18, 1981.
Schwarz and Beaty, Chapter eleven: Propagation from Non-meristematic Tissues—Organogenesis, CRC Press, pp. 95–104, 1996.
Douglas, G.C., Chapte 8: Manipulation of Shoot Formation in Cultured Explants, Methods in Molecular Biology, vol. 6, Plant Cell and Tissue Culture, The Humana Press, pp. 71–79, 1990.
Ritchie et al, How a Corn Plant Develops: Special Report No. 48, Iowa State University of Science and Technology, pp. 1–21, 1986.
Pierik, In Vitro Culture of Higher Plant, Martinus Nijhoff Publishers, pp. 1–6, 291, 1987.
Pareddy et al, Maize Transformation via Helium Blasting, Maydica 42:143–151, 1997.
Brown and Thorpe, Chapter 2: Plant Regeneration by Organogenesis, Cell Culture and Somatic Cell Genetics of Plants, vol. 3, Academic Press, Inc., pp. 49–65, 1986.
Dodds and Roberts, Experiments in Plant Tissue Culture, chapter 6: Organogenesis, Cambridge University Press, pp. 82–91, 1995.
Dodds and Roberts, Experiments in Plant Tissue Culture, chapter 10, Micropropagation by bud proliferation, Cambridge University Press, pp. 126–135, 1995.

Southgate et al, A Comparison of Methods for Direct Gene Transfer into Maize (*Zea mays* L.), In Vitro Cell. Dev. Biol.—Plant 34:218–224, 1998.
Raven et al., Biology of Plants, sixth edition, W.H. Freeman and Company Worth Publishers, p. 611, 1999.
Levetin and McMahon, Plants and Society, McGraw–Hill, pp. 43–44, 1981.
Biotechnology, vol. 11, pp. 596–598, May, 1993, Dennis E. McCabe, et al., "Transformation of Elite Cotton Cultivars Via Particle Bombardment of Meristems".
Plant Cell Reports, 8:586–589, (1990), John J. Finter, et al., "Transformation of Cotton (*Gossypium hirsutum* L.) Via Particle Bombardment".
Plant Molecular Biology Reporter, 13 (1) 1995, pp. 31–37, Caryl A Chlan, et al., "A Procedure for Biolistic Transformation and Regeneration of Transgenic Cotton from Meristematic Tissue".
Plant Molecular Biology 10:105–116 (1987), Ebrahim Firoozabady, et al., "Transformation of Cotton (*Gossypium hirsutum* L.) by Agrobacterium Tumefaciens and Regeneration of Transgenic Plants".
In Vitro Cell. Dev. Biol. 29 P:166–173, Oct., 1993, E. Firoozabady, et al., "Plant Regeneration via Somatic Embryogenesis in Many Cultivars of Cotton (*Gossypium hirsutum* L.)".
Critical Reviews in Biotechnology, 17(3): 185–208 (1997), Mmaliyakal E. John, "Cotton Crop Improvement Through Genetic Engineering".
Plant Cell Reports (1997) 16:647–652, D.C. Agrawal, et al., "In Vitro Induction of Multiple Shoots and Plant Regeneration in Cotton (*Gossypium hirsutum* L.)".

*Primary Examiner*—David T. Fox
*Assistant Examiner*—Anne Marie Grünberg
*Attorney, Agent, or Firm*—Piper, Marbury Rudnick & Wolfe, LLP; Steven B. Kelber

[57] ABSTRACT

Maize tissue may be regenerated from nodal extracts prepared from germinated mature seeds and germinated embryos. Nodal section explants are secured from seedlings in 3–5 days. The explants are grown on an induction medium until adventitious shoot formation is observed. The shoots are separated and elongated on an MS-based medium, and then rooted. Fast genotype-independent regeneration is obtained, in 12–14 weeks. These explants, as well as zygotic embryos, may be transformed with exogenous DNA using a biolistic approach, where DNA precipitated onto tungsten microprojectiles is accelerated as 650 psi towards the explants at a distance of at least 7.5 microns. Improved frequency of transformation is obtained using microprojectiles which prior to DNA precipitation were frozen in glycerol, and suspending from a preparation of 2.5 M $CaCl_2$. The combination of transformation process and regeneration can be used, independent of genotype, to provide new commercial crop organisms.

13 Claims, No Drawings ical material such as deoxyribonucleic acid (DNA) into living organisms. Genetic transformation is a process which simply involves the uptake of foreign DNA by somatic cells of an organism. It is an unique mechanism by which foreign DNA of any origin (bacterial, animal, plant . . . ) is stably incorporated into the host genome. As a result, the introduced DNA becomes a part of the parent genome inflicting a permanent genetic change and can be inherited by the subsequent progeny, Chibbar and Kartha, 1994. Such human-engineered organisms harboring additional genetic information are called "transgenic organisms", be they plants or animals, Dekeyser et al., 1990.

METHODS FOR MAIZE TRANSFORMATION COUPLED WITH ADVENTITIOUS REGENERATION UTILIZING NODAL SECTION EXPLANTS AND MATURE ZYGOTIC EMBRYOS

This application is a regular National application claiming priority from Provisional Application, U.S. application Ser. No. 60/048,678 filed Jun. 6, 1997. The entire disclosure of this Provisional Application is incorporated herein by reference.

BACKGROUND OF THE INVENTION

Introduction

Recent advances in genetic engineering have given new impetus to crop improvement. Major breakthroughs have been achieved via development of genetic transformation techniques that facilitate introduction of heritable material such as deoxyribonucleic acid (DNA) into living organisms. Genetic transformation is a process which simply involves the uptake of foreign DNA by somatic cells of an organism. It is an unique mechanism by which foreign DNA of any origin (bacterial, animal, plant . . . ) is stably incorporated into the host genome. As a result, the introduced DNA becomes a part of the parent genome inflicting a permanent genetic change and can be inherited by the subsequent progeny, Chibbar and Kartha, 1994. Such human-engineered organisms harboring additional genetic information are called "transgenic organisms", be they plants or animals, Dekeyser et al., 1990.

Plant transformation techniques involving different systems of gene transfer have been a boon to plant breeders to introduce variability at the molecular level, Cocking and Davey, 1987, and thereby increase genetic diversity, Barton and Brill, 1983. It has helped in the creation of genotypes with novel traits. The recently released, extended shelf-life Flavr-Savr™ tomatoes, Redenbaugh et al., 1992, transgenic Bt-cotton containing resistance to the cotton boll worm, Perlak et al., 1990, and many other such examples, have helped mankind save on costs due to fruit rot and insect control, to name a few. Therefor, transgenic plants could potentially provide an economic edge over conventionally bred crop species in terms of being environmentally friendly, in reducing the risks from using hazardous pesticides and herbicides, in addition to bolstering yields either directly or indirectly, Gasser and Fraley, 1992.

Although more is known about its genetics than many other crops, and despite extensive breeding efforts, maize (Zea mays L., Poaceae) as a crop, still requires continual genetic improvement. Examples include developing resistance (or tolerance) to diseases, pests, and herbicides, and improving the protein quality, all of which contribute to increased net economic gain. Great emphasis has been placed on maize breeding for crop improvement, Chassan, 1992, due to its extreme value as a cereal crop worldwide. In fact, it ranks as the world's third largest crop, trailing only behind wheat and rice, Langer and Hill, 1991. In the United States, it is the leading cereal (grain) crop and in 1995, 3,351,762 metric tonnes were produced on 26,314 hectares and was valued at greater than $23 billion, U.S., U.S. Department of Agriculture-National Agricultural Statistics Service, 1995–96. Due to the importance of maize in the U.S. and worldwide, many maize improvement programs are currently utilizing genetic engineering protocols to complement/enhance classical breeding efforts which are limited to working with genes (traits) already present in the maize germplasm.

The biolistic system has certain unique advantages over other gene transfer systems. It is very simple to operate and has universal applications because it can be used for gene transfer into cells of plants, animals, or microbes, Klein et al., 1992. Since its advent, it has been a very useful method commonly employed to transform the world's cereal crops like rice, barley, sorghum, oat, wheat and maize, Christou et al. 1991; Klein et al., 1989; King et al., 1994; Ritala et al., 1994; Somers et al., 1992; Vasil et al., 1994. The biolistic process has since proven to be the best available system for transforming monocots, Batty and Evans, 1992.

Regeneration of maize involves the use of juvenile tissues by employing explants or tissues derived from seeds either pre- or post-germination. Successes have been limited to the use of embryogenic calli maintained in suspension cell culture (e.g. BMS and other elite inbred lines) initiated from immature embryos, and whole immature embryos as targets for developing biolistics-based transformation systems for maize, Gordon-Kamm et al., 1990; Fromm et al., 1990; Walters et al., 1992; Lowe et al., 1995. Ideal target tissues would be capable of accepting foreign DNA at high frequencies and regenerating plants (hopefully transgenic) efficiently.

Optimization must be conducted for each explant/tissue type and is usually based on the transient expression of the introduced genes. Transient expression refers to the expression of gene sequences that may or may not be integrated into the host genome and are usually conducted after a brief (42–72 h) post-bombardment period. Transient expression frequencies provide rapid and useful information as to whether foreign DNA was introduced or not. In addition, correlations can be made to stable transformation frequencies. Researchers estimate the stable transformation frequency to be from less than 1% up to 5% of the transient expression frequencies, Finer and McMullen, 1990; Klein et al., 1988b. Thus, transient expression has proven to be a very useful indicator of DNA delivery and is routinely used in investigating the optimum conditions required to deliver DNA into different explant/tissue types via biolistics. For many crop species, optimization of bombardment (DNA delivery) is conducted by measuring the transient expression of the reporter gene, β-glucuronidase (GUS), by a histochemical assay, 48–72 h post-bombardment, Jefferson et al., 1987.

It is evident that development of regeneration protocols for various target tissues and optimization of critical biolistic parameters utilizing these tissues assume great importance in developing a biolistics-based transformation system for maize.

Literature Review

Maize Tissue Culture

Maize has been regenerated in vitro by following different systems of regeneration. These include regeneration via somatic embryogenesis and organogenesis with both utilizing adventitious (including de novo) regeneration protocols, Vasil, 1986.

Maize Regeneration from Different Explant Sources

Immature Zygotic Embryos as Explants for Callus Cultures

The successful induction of somatic embryogenesis, maturation and germination of embryoids into plantlets are dependent on a number of variables. They include: genotype, age of the extracted immature zygotic embryos (days post-pollination; dpp), sucrose concentration in the media, the plant growth regulators (PGRs) utilized along with other media additives and associated culture conditions. Table 1 lists the genotypes successful in plant regeneration utilizing immature zygotic embryos as explants. Regeneration was a result of scutellar tissue proliferation which lead to the formation of embryogenic callus from which mature bipolar somatic embryos emerged and subsequently, regenerated into whole plantlets.

picloram, 150 mg/l L-asparagine incubated under continuous light conditions at 28° C. Shoot differentiation occurred on a MS-based medium containing 25% (w/v) sucrose and 10 mg/l kinetin under increased light intensity (10,000 lux).

TABLE 1

Plant regeneration via somatic embryogenesis from the scutellum of immature zygotic embryos.

| Genotype/ Cultivar | Plant Growth Regulators (PGRs) | | | Reference |
|---|---|---|---|---|
| | Induction Medium | Maturation Medium | Gemination Medium | |
| A188 | 2,4-D[z]: 2.0 mg/l | 2,4-D: 0.25 mg/l | PGR-free | Green & Phillips, 1975 |
| A188 X R-njR-nj | | | | |
| B73 | 2,4-D: 0.5 mg/l | PGR-free[y] | PGR-free | Lowe et al. 1985 |
| Silver Queen | 2,4-D: 0.5 mg/l | PGR-free | $GA_3^{x:\ 1.0\ mg/l}$ | Lu et al. 1982 |
| Asgrow Rx112 | 2,4-D: 0.25–1.0 mg/l | PGR-free | PGR-free | Lu et al. 1983 |
| Coker 16 | | | | |
| Coker 22 | | | | |
| Dekalb XL80 | | | | |
| Dekalb XL82 | | | | |
| Florida Stay Sweet | | | | |
| Furtk G4864 | | | | |
| Furtk G4507A | | | | |
| Pioneer 3030 | | | | |
| Pioneer 3320 | | | | |
| Silver Queen | | | | |
| Dekalb XL 82 | 2,4-D: 0.5–1.0 mg/l | | ABA[s]: 0.02 mg/l | Vasil et al. 1985 |
| A188 | 2,4-D: 1.0 mg/l L-proline: 690 mg/l | PGR-free | PGR-free | Armstrong & Green, 1985 |
| Mo17 | 2,4-D: 1.0 mg/l | BAP[w]: 3.5 mg/l | PGR-free | Duncan & Widholm, 1988 |
| Pa91 | L-proline: 1.38 mg/l | $AgNo_3^t$: 34 mg/l | | |
| R99 | | | | |
| A188 | 2,4-D: 1.0 mg/l | | NAA[v]: 1.0 mg/l & 2iP[u]: 0.05 mg/l | Torne et al. 1984 |
| H-fl₂ | | | | |
| H-113 | | | | |
| V444 | | | | |
| W64A₀₂₀₂ | | | | |
| A188 | 2,4-D: 1.0 mg/l | PGR-free | PGR-free | Duncan et al. 1985 |
| A658 | | | | |
| B79 | | | | |
| H60 | | | | |
| H97 | | | | |
| H99 | | | | |
| L317 | | | | |
| Oh7 | 2,4-D: 1.0 mg/l | PGR-free | PGR-free | Duncan et al. 1985 |
| Pa91 | | | | |
| R806 | | | | |
| Wf9 | | | | |
| W64A | | | | |
| A634 X A188 | 2,4-D: 0.5 mg/l | PGR-free | PGR-free | Hodges et al. 1986 |
| A632 X A188 | | | | |
| B73 X A188 | | | | |
| B14 X A188 | | | | |
| B68 X A188 | | | | |
| CM105 X A188 | | | | |

[z]Gibberellic acid
[y]Plant growth regulator-free
[x]2,4-dichlorophenoxyacetic acid
[w]6-benzylaminopurine
[v]α-naphthaleneacetic acid
[u]6-(γ,γ-dimethyl allylamino)-purine
[t]silver nitrate
[s]Abscissic acid Seedling Nodal Tissues as Explants Seedling nodal tissues from inbred B73 were excised from dark-grown, 3–4 day old germinated seedlings (obtained from mature seeds) and used to initiate organogenic callus cultures, Lowe et al., 1985. Nodal tissues were placed on a MS-based medium, Murashige and Skoog, 1962, containing 2% (w/v) sucrose, 0.5 mg/l 2,4-D, 3.0 mg/l The shoots were transferred to a MS-based medium with 2% (w/v) sucrose and 0.1% (w/v) charcoal for rooting, Lowe et al., 1985.

TABLE 2

Plant regeneration via somatic embryogenesis from other tissues established from immature zygotic embryos
Plant Growth Regulators (PGRs)

| Explant Type | Genotype/ Cultivar | Induction Medium | Maturation Medium | Germination Medium | Reference |
|---|---|---|---|---|---|
| Mesocotyl | Homozygous $fl_2$ | 2,4-D: 1.0 mg/l | NAA: 1.0 mg/l & 2iP: 0.05 mg/l | PGR-free | Torne et al., 1980 |
| Nodal Region | Asgrow Rx112 Coker 16 Coker 22 Dekalb XL80 Dekalb XL82 Florida Stay Sweet Funks G4507A Pioneer 3030 Pioneer 3320 Silver Queen | 2,4-D: 0.25–1 mg/l | 2,4-D & BAP or Kinetin: 0.1 mg/l | PGR-free | Vasil et al. 1983 |
| Protoplasts | B73 | 2,4-D: 0.5 mg/l | 2,4-D: 0.25 mg/l Kinetin: 15 mg/l | PGR-free | Shillito et al., 1989 |
|  | A188 and B73 | 2,4-D: 1.0 mg/l | PGR-free | PGR-free | Rhodes et al. 1988 |

Shoot Tip Apices as Explants

Raman et al., 1980, established shoot tip cultures as a method of maize propagation for eight genotypes (Table 3). Stem segment explants, which consisted of the shoot apical meristem plus a few axillary bud primordia were excised from the scutellar region of 20 day old seedlings obtained from greenhouse grown maize. Those explants were used to enhance axillary bud proliferation (perhaps adventitious in nature) and developed maximum numbers of shoots when placed on a MS-based medium, Murashige and Skoog, 1962, containing 3% (w/v) sucrose, adenine sulfate dihydrate (120 mg/l), kinetine (3.0 mg/l) plus IAA or IBA (1.0 mg/l). It was determined that cytokinins alone did not stimulate axillary bud break/proliferation. NAA (5.0 mg/l) added to the basal medium (minus other PGRs) stimulated rooting of the excised shoots. In addition to genotypic differences in regeneration capacity, phenotypic abnormalities were noted in regenerated plantlets from all genotypes, Raman et al., 1990.

Somatic embryos and adventitious shoots were regenerated from shoot tips of maize seedlings and precociously germinated immature zygotic embryos from 18 genotypes, Zhong et al., 1992; Table 3. Mature seeds or immature zygotic embryos (10–15 dpp) were placed on numerous media in a step-wise manner, first on a MS-based, Murashige and Skoog, 1962, medium (A) containing sucrose (concentration not mentioned) and 500 mg/l of casein hydrolysate (CH) to achieve germination. After 7 days, the shoot tip explants were excised and placed on medium A plus 2.0 mg/l BAP for four weeks, then transferred to A containing 0.5 mg/l 2,4-D plus 2.0 mg/l BAP for four weeks to form adventitious shoots. For somatic embryo production, the cultures would then be transferred to A containing 0.5 mg/l BAP. Further organogenic shoot development also occurred on this same medium with rooting accomplished on A containing 0.87 mg/l IBA, Zhong et al., 1992. Explants from immature tassels and immature ears obtained from greenhouse-grown sweet corn hybrid Honey N Pearl plants could also initiate shoots on various media. Clumps of multiple shoots were regenerated from immature ears within four weeks when cultured on medium A supplemented with 2.0 mg/l BAP, and shoots formed on immature tassel explants when cultured on A containing 0.1 mg/l 2,4-D plus 1.0 mg/l BAP, Zhong et al., 1992.

TABLE 3

Plant regeneration from tissues established from shoot tip apices of maize.

| Explant | Genotype/Cultivar | Reference |
|---|---|---|
| Stem segments from the scutellar region | Oh. 43 Seneca 60 Stewarts 2501 Univ. of W. Ontario accessions 1928 13037 13534 W 23 W 64A | Raman et al., 1980 |
| Shoot apices | Honey N Pearl Michigan genotypes 420 466 482 509 579 582 5922 Illinois genotypes B73 B84 Cm 105 FR 634 FR 632 PRM 017 M79 PA 91 VA22 Minnesota genotype A188 | Zhong et al., 1992 |
| Shoot apices | W23 B73 | Irish & Nelson, 1988 |

Biolistics: History and Development

Introduction of micro-projectiles into tissues at high velocities were first used by plant virologists to mechanically infect plant cells with naked non-infectious viral nucleic acids, as an alternative to spraying the inoculum. These micro-projectiles wounded the plant cells and provided an entry for the viral nucleic acids which then could cause infection, MacKenzie et al., 1966. However, the credit for development of high-velocity micro-projectiles for genetic engineering purposes goes to Drs. J. C. Sanford, T. M. Klein, E. D. Wolf and N. Allen at Cornell University. They developed a number of devices that propelled DNA-coated tungsten micro-projectiles at high velocities into tissues which allowed DNA delivery into plant cells surpassing the cell wall, the primary barrier to DNA introduction. Their systems accelerated micro-projectiles via the following gas discharge, transferred mechanical impulse, macro-projectile plus stopping plate, and centripetal acceleration, Sanford et al., 1987.

The macro-projectile-based system was most promising as it allowed the delivery of micro-projectiles into smaller cell sizes and did not have any detrimental impact on the target cells, Sanford, 1988. The device used a gunpowder charge to accelerate a macro-projectile which carried DNA coated micro-projectiles through a barrel towards a stopping plate. On providing the charge under partial vacuum, the micro-projectiles continued their acceleration into target plant tissues placed in their path. This gunpowder-based acceleration device was called the 'particle gun', Klein et al., 1987; Sanford et al., 1987. The inventors patented a modified version of the particle gun, called a 'biolistic apparatus', Sanford et al., 1989, and the bombardment procedure was referred to as the 'biolistic process', Sanford, 1988. Following their invention, several independent research groups constructed various DNA delivery systems such as the particle inflow gun (PIG; Vain et al., 1993), modified particle inflow gun, Gray et al., 1994, Accell™ technology, McCabe and Christou, 1993, micro-targeting device, Sautter et al., 1991, and the simple particle bombardment device, Brown et al., 1994.

The era of biolistics as a tool for gene transfer was initiated when Klein et al., 1987, demonstrated the delivery of nucleic acids (both RNA and DNA) into living, intact *Allium cepa* L. (onion) cells. Tungsten micro-projectiles (4.0 μm diameter) carrying TMV RNA were "shot" into onion epidermal cells at very high velocities, the first such report for plants, Klein et al., 1987. After bombardment, onion epidermal cells remained viable and those punctured by micro-projectiles coated with TMV RNA produced crystalline inclusions, an indication of the viral nucleic acid expression. Approximately 30–40% of the bombarded onion cells expressed the viral RNA. Onion epidermal tissues were also bombarded with tungsten micro-projectiles (4.0 μm) coated with plasmid DNA encoding CAT, Klein et al., 1987. The CAT coding sequence contained the first intron of Adhl at its N-terminus flanked by CaMV 35S promoter and nos 3' sequence. Three days post-bombardment, transient expression of CAT was demonstrated by using a radioactive precursor with products detected via thin layer chromatography, Klein, et al., 1987.

Sanford et al., 1987, proposed that the use of high velocity micro-projectiles would overcome problems associated with DNA delivery via protoplast-based methods like electroporation. Sanford, 1988, also opined that the biolistic process was an ideal gene delivery system, because DNA delivery was simple and rapid. It allowed transformation of numerous competent cells and tissues of size as small as 5.0 μm in diameter (plant/microbial cells, organelles) with the same basic protocol, irrespective of their shape and cell environment, Sanford et al., 1993. The DNA-coated micro-projectiles dispersed/scattered at random toward the targeted explant/tissues at very high pressures. A lack of uniformity in DNA delivery was inherent with the system. However, DNA delivery with very minimal damage to the target tissue was obtained. The biolistic process was then upgraded by making changes to the macro-projectile and stopping plate of the particle gun, Klein et al., 1987. These changes were incorporated into the gunpowder-based particle delivery system, PDS-1000 (licensed from DuPont with distribution via Bio-Rad), and the most recent helium-driven PDS-1000/He®, Sanford et al., 1989. The gunpowder-based particle gun used nail gun cartridges as the power source, however they were dangerous and left residues from gas and debris within the device. The upgraded helium-driven apparatus was safer and cleaner to use, Sanford et al., 1993.

PDS-1000/He® System for DNA Delivery

The PDS-1000/He® system is the only commercially available particle bombardment device (FIG. 1; Kikkert, 1993). The PDS-1000/He® contained a small, high pressure chamber with a gas acceleration tube that could be blocked by disks that ruptured at pre-set helium gas pressures. Once the pre-set pressure was reached, the helium would quickly enter the target chamber that was maintained under vacuum. The target chamber contained a micro-projectile (microcarrier) launch assembly, which housed the macro-projectile and a stopping screen just beneath it. The helium pressure pushed the macro-projectile (macro-carrier) onto the stopping screen and the exerted force propelled the DNA-coated micro-projectiles off the macro-projectile and onto the target tissues.

During operation of the PDS-1000/He®, in addition to alterations in helium pressure (450–2200 psi), other variables requiring optimization included the gap distance (0.32–1.0 cm; distance between rupture disk retaining cap and launch assembly) and target distance (3–12 cm; distance from stopping screen to target tissues). Higher helium pressures did not necessarily result in higher transformation rates, Sanford et al. 1993. Aside from altering helium pressures under vacuum, the macro-projectile and micro-projectile velocities could also be altered by changing the gap and target distances. In addition, greater distances resulted in the micro-projectiles being scattered over a wider area of the target tissues.

Prior to loading samples onto the macro-projectiles and PDS-1000/He® operation, micro-projectiles of different type and size (gold: 0.6–1.6 μm; tungsten: 0.4–1.7 μm) could be mixed with the chosen DNA ($\geq$ one plasmid type). The amounts of micro-projectiles and DNA used per shot and the number of shots per tissue could also be varied. Although the system was flexible in that many parameters could be varied, each needed to be optimized (in combination with other parameters) for each explant/tissue type to obtain the greatest transient and stable transformation frequencies, Klein et al., 1988c.

Genes for Introduction into Monocots

The vectors or gene constructs used for biolistic experiments should encode appropriate reporter and selectable marker genes capable of expression either constitutively or in specific cell types. Gene constructs used for monocots usually contained monocot promoters and also a monocot intron fused to the N-terminal region of the coding sequences. Monocot introns have been demonstrated to significantly enhance gene expression in monocots, Callas et al., 1987; Vasil et al., 1989; McElroy et al., 1990; Last et al., 1991; Mass et al., 1991 and Donath et al., 1995. Klein et al., 1988a, detected high CAT activity in BMS cells bombarded with pCaMVI$_1$CN harbored the first intron of the Adhl fused to the N-terminal region of CAT controlled by CaMV 35S promoter and nos 3' sequences. Decreased levels of CAT expression were noted when BMS cells were bombarded with pCaMVCN, an identical CAT-based construct except it lacked Adhl intron, Klein et al., 1988a. A construct with the first intron of Adhl fused to the N-terminal region of GUS controlled by the Adhl promoter with nos 3' sequences was demonstrated to enhance GUS expression in suspension cultures of A188×B73 and B73×A188, Fromm et al., 1990.

Higher transient expression rates were noted in suspension cells ot *Panicum maximum* (guineagrass) cv. Pm86, maize (cv. Zm85), *Pennisetum purpureum* (napiergrass) cv.

Pp90, *Pennisetum glaucum* (pearl millet) cv. Pg86, *Saccharum officinarum* (sugarcane) cv. Sc84, wheat cvs. Ta87, TA89, and TA90, and immature embryos of pearl millet following bombardment via the gunpowder-based PDS-1000 when plasmid pAHC25 was utilized versus pBARGUS, Taylor et al., 1993.

Plasmid pAHC25 contained GUS and bar coding sequences driven by maize ubiquitin (Ubi1) promoters and nos 3' with the first intron of Ubi1 fused to N-terminal regions of GUS and bar. Plasmid pBARGUS contained GUS and bar and coding sequences with Adh1 intron 1 fused to each N-terminal region. Flanking regions included Adh1 promoter (GUS), CaMV 35S (bar) and nos 3'. Similar results were obtained in comparisons utilizing three week old embryogenic callus cultures of wheat cvs. Bob White, Pavon and RH770019 following particle bombardment DuPont PDS-1000 or PDS-1000/He®, Vasil et al., 1993.

Superiority of GUS expression in transgenic tissues containing pAHC25 was attributed to the ubiquitin promoter which was constitutively expressed irrespective of the tissue type; while GUS in pBARGUS controlled by the Adh1 promoter was demonstrated to be developmentally regulated, organ specific and up-regulated under anaerobic conditions, Taylor et al., 1993. Ubiquitin-based plasmids were therefor considered superior to the Adh1-based plasmids, Taylor et al., 1993; Vasil et al., 1993. However, studies using *Sorghum vulgare* L., cv. Grazer suspension cultures bombarded with plasmids containing NPTII, hph, and GUS genes driven by the Adh1 promoter determined that the monocot promoter yielded higher transient GUS expression levels compared to those genes driven by CaMV 35S promoter, Mendel et al., 1989.

Suspension cultures derived from immature zygotic embryos of barley, winter type cv. Borwina bombarded with NPTII- and GUS-containing plasmids revealed that plasmid size was also a critical factor to be considered, Hagio et al., 1991. Bombardment with a smaller plasmid (5.1 kilo bases; kb) yielded more stable transformants versus larger ones (12.8 kb and 14.2 kb). However, the amounts of plasmid DNA delivered per shot were not equal with respect to all three plasmids, Hagio et al., 1991.

Transient Expression Quantified by GUS Assays

As mentioned previously, the target explants/tissues were usually bombarded with a reporter gene to measure its expression visually, an easy technique to confirm delivery of the foreign DNA. Initial biolistic experiments conducted by researchers utilized the β-glucuronidase (GUS) gene as a 'reporter' of successful DNA delivery and its gene product was assayed histochemically as 'blue' cells, Wang et al., 1988; Klein et al., 1988c. This proved to be a convenient measure to optimize the gene transfer efficiency in rice, wheat and *Glycine max* (soybean; Wang et al., 1988. The GUS 'blue cell' assay was also successfully used to detect foreign DNA in bombarded tobacco suspension cultures from line XD, Klein et al., 1988b. In deciphering the factors or parameters that influenced gene delivery into BMS suspension cultures via transient expression, Klein and coworkers, 1988c, used GUS to monitor DNA introduction via transient expression assays. The plasmid pAI$_1$-GusN contained the Adh1 promoter, the first intron of Adh1 fused to the 5' end of the GUS coding region and nos 3'. From 1988, the GUS assay formed an integral part of many biolistic experiments in order to optimize the biolistic parameters based on transient expression, to achieve high transformation efficiencies, Klein et al., 1988c.

The expression of GUS was detected histochemically when the bombarded cells were incubated in the presence of a synthetic substrate, 5-bromo-4-chloro-3-indoyl-β-D-glucuronic acid (X-glu). The cells turned blue only when the substrate was cleaved by β-glucuronidase enzymatically, thus confirming the introduction and expression of the GUS gene. The blue color was due to the formation of a precipitate which could be visualized, Jefferson et al., 1987. Some researchers have also used luciferase or anthocyanin genes as reporter genes, King and Kasha, 1994; Goff et al., 1990; Fromm et al., 1990.

In U.S. Pat. No. 5,320,961, Zhong, et al., a method for asexually propagating maize to produce a fertile corn plant is described, in which shoot tip apices isolated from either caryopses or kernels are employed. The explant relied on by Zhong consists of five mm sections of the localized enlargement of the seedling at the junction of the mesocotyl and the leave sheath. The explant described essentially contains the shoot tip, three to five leave primordia and a portion of young leave and stem immediately below the leave primordia. This indicates that the explant employed by Zhong is green (because the seedling is one week old, the localized enlargement would be dark green which gives an indication of its advanced developmental stage; this is a characteristic feature of reduced cell division combined with enhanced cell elongation).

Zhong does not describe the transformation of maize tissue by the introduction of exogenous DNA. To ensure active uptake of exogenous DNA, it is important that the target tissue be in an early developmental stage, such that the tissue is comprised of cells that are in a state of cell division and not cell elongation.

Zhong et al. employ mature seeds or precociously germinated immature zygotic embryos (10–15 days post-pollination) placed in numerous media in a step-wise manner, first on a MS-based medium containing sucrose and casein hydrolysate to achieve germination, followed by the medium further containing 2.0 mg/l 6-benzylaminopurine (BAP). The Zhong process is plant growth regulator (PGR) dependent, and takes about 17–19 weeks to obtain plantlets.

Accordingly, it remains an object of those of skill in the art to provide a method to asexually regenerate maize, and to couple such a regeneration process with a transformation process to introduce exogenous, desirable DNA, which is preferably genotype-independent, and generally applicable to a wide variety of commercially important crops. Accordingly, the regeneration protocol must rely on tissue actively in the state of cell division.

SUMMARY OF THE INVENTION

Regeneration and Transformation of Corn

The corn transformation procedure of this invention integrates a corn multiple shoot induction protocol with nodal sections as explants. Those explants are also used as targets in a biolistics-based transformation system.

Surface Sterilization and Germination of Maize Seeds

Corn seeds are surface sterilized in a solution containing 20% (v/v) commercial bleach and 0.5% SDS for 15 min. under continuous shaking, then serially rinsed in sterile double-distilled water (sddw) four to five times. Liquid MS-based germination medium (CSG) containing MS salts, sucrose (30 g/l), DM-vitamins (1.0 mg/l thiamine-HCl, 0.5 mg/l nicotinic acid, 0.5 mg/l pyridoxine-HCl and 100 mg/l myo-inositol) and BAP (2.0 mg/l) at pH 5.8 is dispensed per Magenta™ box (45 ml) containing eight layers of cheese cloth, then autoclaved. Seeds are placed in CSG (25 seeds of any genotype per box) and cultured for three days (16 h of continuous light; 25° C.) for germination. Nodal section explants (one per seedling) are excised from three day-old seedlings. The nodal section appears as a clear demarcation on the germinating seedling and represents the seventh node. Cuts are made just above and below the node resulting in a 1.2–1.5 mm length cross-section.

Multiple Shoot Induction

Nodal section explants are placed on corn shoot induction medium [CSI; MS salts, sucrose and DM-vitamins same as above, BAP (2.0 mg/l; filter-sterile, incorporated post-autoclaving), CPA (0.25 mg/l; filter-sterile, incorporated post-autoclaving), glycine (10 mg/l) and asparagine (150 mg/l) and phytagar (8 g/l) at pH 5.8], acropetal end up, and placed under the culture conditions previously mentioned. Tissues are subcultured every two weeks onto fresh CSI medium for multiple shoot formation. Adventitious shoots are separated from the shoot clumps after eight weeks and elongated on semi-solid MS-based medium containing sucrose, DM-vitamins, glycine (10 mg/l) and asparagine (150 mg/l) at pH 5.8 for three weeks (FIG. 1E). The plantlets are rooted on the same medium but which also contains indole 3-butyric acid (IBA) (0.5 mg/l). Rooted plantlets can be grown in PGR-free liquid MS in test tubes (150×25 mm) containing cheesecloth as the anchor material to achieve faster growth. Regenerated plantlets are transplanted to potting media, acclimatized, and then grown to maturity in the greenhouse.

Preparation of Tungsten Microprojectiles

Approximately 60 mg of tungsten microprojectiles [M-25 (1.6 μm)] is weighed and placed in a 1.5 ml microcentrifuge tube with 1.0 ml 100% ethanol, then vortexed vigorously for 3 min. The mixture is microcentrifuged for one min., the supernatant discarded and the ethanol wash procedure is repeated twice. The microprojectiles are then resuspended in 1 ml 100% ethanol and placed at room temperature overnight. The following day, the mixture is microcentrifuged for 1 min. The supernatant is removed and the microprojectiles are washed in 1.0 ml sddw and microcentrifuged for 1 min. The supernatant is discarded and the microprojectiles are then resuspended in 1.0 ml sterile 50% (v/v) glycerol yielding a 60 mg/ml stock that can be stored frozen (−20° C.) before use.

Sterilization of Macrocarriers and Rupture Disks

Macrocarriers and rupture disks (650 psi) are sterilized for 15 min in 100% ethanol and dried in the laminar air flow hood and the gene gun parts are sterilized overnight in 70% ethanol. The gene gun is disinfected via a thorough spray of reagent alcohol.

DNA Precipitation onto Tungsten Microprojectiles

On ice, approximately 5 μl (1.0 μg/μl) nuclear transformation vector pAHC25 DNA is added to 60 μl tungsten microprojectiles in a Treff tube. The following are then added: 10 μl isopropanol (2×vol of DNA), 50 μl 2.5M CaCl$_2$ and 20 μl 0.1M spermidine and vortexed for three min. The mix is incubated on ice for three min. then the vortex and incubation steps are repeated. The mixture is then microcentrifuged and the supernatant discarded. The microprojectiles are washed once in 250 μl 70% ethanol and microcentrifuged for one min. The supernatant is discarded and the microprojectiles are resuspended in 60 μl 100% ethanol and vortexed briefly. The DNA loaded microprojectiles can also be maintained frozen pending use.

Approximately 12 μl of the DNA-coated microprojectiles are loaded onto each macrocarrier which delivers 1.0 μg DNA and 720 μg of tungsten per shot. The above mixture is good for five shots.

Bombardment of Nodal Sections

On the day of bombardment, nodal sections are excised and placed, acropetal end up, in the central 2.5 cm area of a petri dish (40 per dish) containing CSI medium devoid of amino acids.

Bombardment Conditions

The following conditions are used to bombard corn nodal section explants: 650 psi helium pressure, gap distance (1.0 cm), and target distance (7.5 cm), with two bombardments per plate using the PDS-1000/He device (Bio-Rad).

Selection of Transgenic Tissues Post-Bombardment

The nodal sections are separated and spread out on CSI medium maintaining polarity and placed in the dark for two days post-bombardment. Histochemical staining for β-glucuronidase expression was conducted three days post-bombardment (FIG. 1C). Explants are then placed on CSI medium devoid of amino acids but contains the selective agent, phosphinothricin at 2.0 mg/l. The regeneration protocol described above is followed to select for green shoots and rooted in the presence of phosphinothricin. Transgenics are confirmed via PCR analysis with appropriate primers specific for the bar and β-glucuronidase sequences.

As will be noted above, and as explained in more detail below, a major difference between the invention addressed herein and that of Zhong is the use of nodal explants excised from 3–5 day old germinated corn seedlings. The nodal section is excised from the area starting at the point of clear demarcation of the node on the seedling and below. Thus, the explant employed is in an early developmental stage, indicating that the tissue (at least 50%) is comprised of cells that are surely in a state of cell division and cell elongation (Kiesselbach, Research Bulletin 161, University of Nebraska (1980)).

Further, in contrast to the regeneration process described in Zhong, plantlets are obtained about 5 weeks earlier, that is, in 12–14 weeks, using a single medium. The medium used to germinate mature seeds is plate growth regulator free.

DETAILED DESCRIPTION OF THE INVENTION

This invention resides in the discovery that novel explant sources, nodal sections excised from germinated embryos and germinated mature seeds, principally characterized by being comprised of cells in a state of cell division, and approximately 3–5 days old can be used to promote regeneration of fertile plants. Simultaneously, the invention herein resides in the development of a process for biolistic transformation which is independent of explant source and genotype. To demonstrate the universal suitability of the biolistic transformation protocol that is one aspect of the invention herein, not only nodal explants of the invention herein, but two other target tissues, including immature zygotic embryos (approximately 13–15 days post pollination or DPP) and mature zygotic embryos were selected as target tissues for biolistic exogenous DNA bombardment. The regeneration of zygotic embryos, and their isolation, per se, as target tissues for transformation, does not constitute an aspect of this invention, and development of protocols to optimize that regeneration are not discussed below. Prior art protocols for these two previously explored target tissues have been developed, and may be equally used. Accordingly, the invention lies in the development of a protocol for regeneration of maize using young nodal sections as explants, coupled with universally applicable biolistic DNA bombardment transformation protocol.

In the experiments described below, a wide variety of parameters are explored, particularly with respect to transformation processes. Many of these parameters are numerically expressed or quantified. Given the need to demonstrate genotype and tissue independence, only so many numerical values may be explored. Nonetheless, the numerical values represent ranges judicially selected about the selected parameters, which ranges appear in the claims appended to this application. The examples provided are not intended to be limiting, and the ranges recited are based on experimental observation, coupled with prior experimentation in related protocols and plants.

In the discussion set forth below, regeneration from nodal sections is first discussed. Having established that nodal explants from germinated embryos and germinated mature seeds can be effectively regenerated into fertile plants, DNA transformation techniques are then explored. In practice, the nodal explant targets are selected, transformed, and regenerated, to give new and improved maize genotype/phenotype crops.

Materials and Methods

All experiments were conducted in a sequential order, in that the cell/tissue culture and regeneration protocols were first developed followed by optimization of gene delivery using the PDS-1000/He®. Tissue culture protocols were established utilizing nodal sections each composed of explants from two different developmental/physiological stages. They included nodal sections excised from aseptically germinated seedlings excised from mature seeds or from germinated immature zygotic embryos.

Maize seeds of all genotypes were provided by Dr. W. P. Williams (Supervisory Research Geneticist, USDA-ARS, Starkville, Miss.). Seeds were field-planted and also grown in greenhouses during the off-season to obtain explants (immature zygotic embryos) for the experiments. Field/greenhouse space and maize production assistance were provided by Dr. W. P. Williams (USDA-ARS) and Dr. Brian S. Baldwin (Assistant Professor, Department of Plant and Soil Sciences, Mississippi State University). Twenty-one different genotypes of maize including 16 grain hybrids, one sweet corn hybrid and four inbreds were used for confirmation of all developed protocols. Table 5 provides the list of genotypes evaluated in optimization of regeneration and used for optimization of gene delivery via PDS-1000/He®.

TABLE 5

Maize genotypes evaluated in culture.

|  | Genotype | Designation |
|---|---|---|
| Grain hybrids | Agratech 810 | A810 |
|  | Agratech 888 F$_4$ | A888 F$_4$ |
|  | Asgrow Rx897 | Arx897 |
|  | Asgrow Rx899 | Arx899 |
|  | Cargill X9255 | CarX9255 |
|  | Cargill 8327 | Car8327 |
|  | Dekalb 649 | DK649 |
|  | Dekalb 683 | DK683 |
|  | ICI 8281 | ICI8281 |
|  | Northrup King 7787 | Nk7787 |
|  | Northrup King 8811 | Nk8811 |
|  | Pioneer 3085 | P3085 |
|  | Pioneer 3145 | P3145 |
|  | Pioneer 3156 | P3156 |
|  | Pioneer 3167 | P3167 |
|  | TR 1185 | TR1185 |
| Sweet corn hybrid | Funks G90 | Funks G90 |
| Inbreds | Mp708 | Mp708 |
|  | Sc229-1 | Sc229-1 |
|  | Sc229-2 | Sc229-2 |
|  | Tx601 | Tx601 |
|  | Va35 | Va35 |

Immature Ear Production in the Greenhouse

Greenhouse plantings were undertaken at two different locations, at the USDA greenhouse (located near the Boll Weevil Research Unit, Starkville, Miss.) and at the Plant Science Research Center (PSRC), Mississippi Agricultural and Forestry Experimental Station (MAFES) greenhouse (North farm, Mississippi State, Miss.).

In the USDA greenhouse, the initial planting occurred in early October 1995. Four maize seeds were planted per 9.45 liter plastic pot containing a potting mix with equal parts of sand and Bacto potting media, then thinned to retain one plant per pot. Two pots per genotype were maintained for all 21 genotypes. Subsequent plants (two plants per genotype) were staggered for adequate pollen supply. The greenhouse temperature was maintained between 23–31° C. Sodium vapor lights in the greenhouse provided the light intensity required for growth and development of maize. A 12 h photoperiod was maintained until the plants tasseled and produced ears. The plants were initially watered twice daily then once per day, and fertilized two weeks post-emergence and every four weeks after establishment with 14-14-14 osmocote time-released fertilizer (2.0 g per application). Insect-control sprays were undertaken on an as-needed basis using Dipel for lepidopteran pests and Knox Out (Diazinon aerosol) for aphid control.

In the MAFES-PSRC greenhouse, the plants for all 21 genotypes were initiated in late February 1996. The maize seeds were planted in 7.56 liter plastic pots containing a mixture of sand, potting soil and ERTH Food (ERTH Group Inc., 1:1:1). The greenhouse temperature was maintained at 28±3° C. Four seeds per pot were initially planted and thinned to one plant per pot, post-germination. Two plants were maintained per genotype for all 21 genotypes. Subsequent plants (two plants per genotype) were staggered. No external lighting was provided and watering was once per day. The plants were first fertilized after emergence at the 3–4 leaf stage and every 15 days with 200 mg/l of ammonium nitrate until maturity and harvest.

Maize seeds in the USDA field trials (MAFES-PSRC, North farm) were planted in April 1996 in rows of 406 cm. Each hybrid/inbred was planted as a separate designated row. Approximately 15 plants were maintained per row with 96.5 cm spacing between each row. The field was supplied with a basal nitrogen dose of 110 kg/ha. Herbicides, Dual (metolachlor) and atrazine at 2.5 kg/ha each were also incorporated to achieve weed control. The field was irrigated in furrows at weekly intervals only if rains were not received. Another top dress of nitrogen (168 kg/ha) was supplied 40 days post-planting. Linuron, a post emergence-herbicide was applied 65 days after planting (1.7 kg/ha).

Hand-Pollination and Harvest

The plants were monitored closely for initiation of tassels and silks. The ear shoots were covered with white paper bags prior to silk emergence. When the tassels dehisced and pollen and silks were receptive to pollen, tassels were covered with brown paper bags and plants were self-pollinated by following standard hand pollination procedures. Hand pollination was done in the morning hours between 8:30 to 11:30 a.m. to ensure good kernel set. The tassels of a genotype were shaken completely within the brown paper bag to facilitate the release of pollen. The pollen in the bag was dropped onto the stigma (on one or two silks) of the same genotype (white bag off), then covered with the brown bag and stapled at the bottom carefully to avoid any foreign pollen contamination. Ears were allowed to develop within the brown paper bags following pollination (date noted on bag). The ears were allowed to develop only for a restricted period of time following self-pollination. Ears were harvested 12, 14 and 18 days post-pollination (dpp). Immature cobs were either used to extract embryos that were placed in culture immediately or stored in a refrigerator at 4° C. for up to three weeks for further use in experimentation.

Media Composition and Culture Conditions

The media composition and culture conditions varied depending on the explant type and the regeneration type desired. All media used in the experiments contained either full strength MS, Murashige and Skoog, 1962, or N$_6$, Chu et al., 1975, basal salts (4.3 g/l or 4.0 g/l respectively; Sigma), DM-vitamins (1.0 mg/l thiamine-HCl, 0.5 mg/l nicotinic acid, 0.5 mg/l pyridoxine-HCl, and 100 mg/l myo-inositol) with varying sucrose concentrations but constant phytagar concentration [0.8% (w/v); GibcoBRL]. Some media contained filter-sterile amino acids L-proline (Sigma), glycine (Sigma) and L-asparagine (Sigma) which were incorporated into the medium after autoclaving. Stock solutions of L-proline (700 mg/ml), glycine (10 mg/ml) and L-asparagine (150 mg/ml) were prepared accordingly and filter-sterilized with a 0.2 μm filter (Sterile Acrodisc®, Gelman Sciences) and stored at 4° C. All media were adjusted to the desired pH prior to autoclaving and the pH of the media varied with regeneration type. All media were autoclaved for 35 min. at 121° C. and 100 kPa pressure. Filter-sterile PGRs were incorporated into the media after autoclaving. Each petri plate (100×20 mm, Nunc) contained approximately 20 ml of medium. The stock solutions of PGRs [2,4-D, BAP, zeatin, kinetin, 4-chlorophenoxyacetic acid (CPA), and $GA_3$] were prepared at 1.0 mg/ml, filter-sterilized using a 0.2 μm filter and stored at 4° C. or −20° C. Depending on the type of regeneration, the cultures were either incubated in the dark at room temperature or in a Percival growth chamber (model 135LLVL, Iowa) under cool white fluorescent lights with a light intensity of 52 $\mu Em^{-2}s^{-1}$, maintained at a 16 h photoperiod with 25/23° C. (internal) day/night temperatures.

Experiments

Adventitious Shoot Organogenesis from Nodal Sections

Adventitious shoot regeneration in maize via proliferation of the shoot apex has been achieved by Raman et al., 1980, and Zhong et al., 1992. IAA or IBA (1.0 mg/l) plus kinetin (3.0 mg/l) in a MS-based medium, Murashige and Skoog, 1962, induced adventitious shoot formation in eight greenhouse-grown genotypes, Raman et al., 1980, but regenerated plants were associated with epigenetic variations. Zhong et al., 1992, reported formation of multiple adventitious shoots from 17 genotypes using shoot-tip apices from maize seedlings, and precociously germinated immature zygotic embryos on a multi-step MS-based medium containing BAP (2.0 mg/l) as the initial medium.

Before establishing the adventitious regeneration protocol, it is important to establish surface-sterilization and germination protocols for mature seeds to obtain two different sources of young, healthy maize seedlings. Those would be the donor sources for excision of juvenile nodal sections (one section per seedling) that would serve as explants for adventitious regeneration. Genotype-independent adventitious regeneration protocols exhibiting minimal phenotypic variation would be highly desirable to use in combination with biolistic transformation protocols. Use of nodal sections excised from immature or mature seedlings as target tissues have not been reported previously.

Maturation and Germination of Immature Zygotic Embryos

Immature zygotic embryos from the maize genotypes, Honey N Pearl and B30000 were matured on a MS-based maturation medium containing 15% (w/v) sucrose, 0.5 mg/l zeatin and 1.0 mg/l IAA, Lowe et al., 1995. This maturation protocol was changed with respect to the PGRs in the medium and wanted to determine which of three high sucrose concentrations enhanced the maturation process. This study was initially conducted with four genotypes, Dekalb 683, Pioneer 3085, Pioneer 3156 (commercial hybrids), Sc229-1 and Sc229-2 (inbreds). The maturation medium tested was full strength MS-based and contained DM-vitamins, and phytagar (8.0 g/l). Three different sucrose concentrations, 12%, 15% and 17% (w/v) were incorporated into this basal medium. All media were adjusted to a pH of 5.8 prior to autoclaving and autoclaved as previously noted. The maturation media designations according to the sucrose composition are given in Table 7. Filter-sterile kinetin (0.5 mg/l) was added to each medium before pouring to 100×20 mm petri plates following autoclaving. The experiment was conducted in a completely randomized design, with each petri plate containing 15 immature zygotic embryos (12–14 dpp) which formed an experimental unit, with three replicates per treatment. The cultures were incubated in the dark at room temperature for one week and later moved to the growth chamber and placed under a 16 h photoperiod at 25/23° C. (internal) for one week, during which the coleoptiles emerged and the scutellar node was evident.

TABLE 7

MS-based media tested for maturation of immature zygotic embryos (12–14 dpp)

| Sucrose % | Media Designation |
|---|---|
| 12 | $M_1$ |
| 15 | $M_2$ |
| 17 | $M_3$ |

Surface Sterilization of Mature Seeds

Approximately 30 seeds from each genotype were surface-sterilized separately in a solution containing 20% (w/v) commercial bleach and 0.5% SDS solution for 15 min. in a sterile 250 ml conical flask. The seeds were shaken vigorously every 5 min. to ensure complete soaking in the bleach-SDS solution. After 15 min., the bleach-SDS solution was drained off and the seeds were serially rinsed in sddw four to five times. The same protocol was followed for surface sterilization of mature seeds for all genotypes. Surface disinfested seeds were placed onto plates (100×15 mm) containing MS-0 medium (PGR-free) to allow germination. The plates were placed under a 16 h photoperiod, in the growth chamber 25/23° C. for five days.

Adventitious regeneration from the nodal sections of young seedlings and germinated embryos was then explored. Varying concentrations of 4-chlorophenoxyacetic acid (CPA) or 2,4-D in combination with BAP in a full strength MS-based medium were tested for adventitious shoot initiation responses in preliminary experiments. The nodal region of the seedlings from immature zygotic embryos and mature seeds were utilized. The full-strength MS-based media containing DM-vitamins, 10 mg/l glycine, 150 mg/l asparagine, sucrose (3%; w/v), phytagar (0.8%; w/v), and 2.0 mg/l BAP, with varying levels of CPA and 2,4-D are listed in Table 8. These media differed with respect to their auxin concentration and amino acid composition from that reported by Zhong et al., 192, for shoot-tip apices. Each medium was adjusted to a pH of 5.8 prior to autoclaving. Filter-sterile amino acids and PGRs were incorporated into the media after autoclaving as described previously. Five genotypes, Dekalb 683, Pioneer 3085, Pioneer 3156 (commercial hybrids), Sc229-1 and Sc229-2 (inbred lines) were evaluated on the six different media.

Following maturation, immature zygotic embryos germinated into seedlings on the maturation medium $M_2$, from which approximately a 3.0–4.0 mm (length) and approximately 1.2–1.5 mm diameter section of the scutellar node (that formed a characteristic ridge-like protrusion) was excised.

TABLE 8

Media designations with auxin composition (plus BAP at 2.0 mg/l) used for adventitious shoot development from nodal section explants.

| Auxin type | Concentration (mg/l) | Medium Designation |
|---|---|---|
| CPA | 0.25 | A |
| CPA | 0.50 | B |
| CPA | 0.75 | C |
| 2,4-D | 0.25 | D |
| 2,4-D | 0.50 | E |
| 2,4-D | 0.75 | F |

The scutellar node from aseptically germinated seedlings (arose from mature seeds) also appeared as a prominent ridge and was excised (2.5–3.0 mm in length; 1.5–2.0 mm in diameter). Scutellar nodal sections from each source were placed on the six media previously described. Five nodal sections per plate constituted an experimental unit with three replicates per treatment. Four genotypes (commercial hybrids: Dekalb 683, Pioneer 3085, Pioneer 3156 and inbreds: Sc229-1 and Sc229-2) were initially tested with a completely randomized experimental design. Observations such as type and quality of shoots initiated were noted after four weeks, and number of shoots formed per explant were noted following eight weeks of culture, just prior to separation of shoots for rooting. Following preliminary screening of the six media with five genotypes, the media were narrowed down to two. Two media, A and D were utilized to test the two nodal section types from all 22 genotypes. Adventitious shoots that formed were separated and placed on a full strength PGR-free MS-based medium containing DM-vitamins, sucrose (3%; w/v), 10 mg/l glycine, 150 mg/l asparagine, phytagar (0.8%; w/v) for three weeks. (Filter-sterile amino acids were incorporated into the medium after autoclaving). The elongated shoots were separated and placed on the same basal medium containing 0.5 mg/l IBA to achieve rooting. The rooted plants were placed in PGR-free liquid MS in test tubes (100×25 mm) containing cheese-cloth as anchor material to achieve faster growth. Three regenerated plantlets from the five pre-screened genotypes were transplanted to pots containing sterile soil mix and acclimatized by potting them in plastic pots containing a sterile potting soil mix, covered with a plastic bag and placed in 6 Dorman Hall for growth at room temperature and 16 h photoperiod. The bag remained closed for seven days. The humidity within the bag was then gradually reduced by making holes in the bag over the next seven days, and eventually the bag was removed. The hardened plants (4–6 leaf stage) were transplanted to 9.45 liter pots containing a mixture of sand, potting soil and ERTH Food (1:1:1) and grown in the MAFES-PSRC greenhouse.

Optimization of the Biolistic Parameters

The optimized precipitation and bombardment procedures described below were determined by testing each variable individually in preliminary experiments that utilized the four genotypes used in all pre-screening: Dekalb 683, Pioneer 3085, Pioneer 3156, Sc229-1 and Sc229-2. Variables included tungsten micro-projectile size and quantity delivered per shot, $CaCl_2$ and DNA concentration, and helium pressure and gap distance used for bombardment. Target tissues used for bombardment purposes included nodal sections [excised from 5 day old germinated embryos (matured in vitro) and germinated mature seeds].

On the day of bombardment, the target tissues were placed on their respective culture media in the central 2.5 cm area of the petri plate. The tissues were not subjected to any kind of pre-culture. Nodal sections derived from germinated immature embryos or mature seeds (40 sections) were placed at the center of the plate in the form of a circle with a 2.5 cm diameter. Five replicate plates of each tissue type per genotype were utilized, of which three replicates were bombarded with pAHC25 DNA and two with pBI101.2 DNA (negative control). All plates were bombarded with a pre-set target distance of 7.5 cm which was never altered.

Post-bombardment, all plates were wrapped with nesco-film (Nescofilm Japan) and placed in the dark at room temperature for three days, then assayed for GUS expression. All optimized variables were determined post-bombardment via transient GUS expression assays, detected histochemically (mean number of blue sectors per explant). Once optimized, target tissues from each of the 21 genotypes were tested via those optimized protocols and evaluated by transient GUS histochemical assays.

The GUS assay has been an integral part of bombardment experiments on maize and other plant species to evaluate important biolistic parameters based on transient expression of the GUS gene via histochemical assays, Wang et al., 1988; Klein et al., 1988b. We analyzed DNA introduction into target cell nuclei via GUS histochemical assays, Jefferson, 1987; Gallagher, 1992, conducted three days post-bombardment for the four different target tissues to evaluate optimal biolistic variables plus the pre-biolistic DNA-micro-projectile precipitation procedure. Three bombarded target tissues per plate were selected at random and incubated overnight in a 96-well enzyme linked immunosorbant assay (ELISA) plate. The targeted tissues were individually placed in the wells each containing approximately 350 μl of the following solution: 0.1 M sodium phosphate, 10 mM EDTA, 0.5 mM potassium ferrocyanide, 0.5 mM potassium ferricyanide, 100 mM X-glu (5-bromo-4-chloro-3-indoyl-β-D-glucuronic acid) and 0.1% (v/v) triton X-100. The tissues were observed for the expression of GUS following overnight incubation at 37 C., Gallagher, 1992.

Plasmid Constructs Used for Bombardment

The plasmid pAHC25 (9.7 kbp; FIG. 2; Christensen and Quail, 1996) was used as a source of foreign DNA. In pAHC25, two marker genes, bar and GUS were each controlled by the ubiquitin promoter (Ubi1) and nos 3' sequences. Each gene contained 5' untranslated sequences [approximately 1.1 kilobase pair (kbp)] which included the first exon and intron from Ubi1. The transcriptional start site ($^+1$) was at the 5' end of Ubi1 exon 1 with the translational start site situated at the beginning of GUS or bar coding sequences (36 bp beyond 3' end of Ubi1 intron 1). The selectable marker gene, bar confers resistance to phoshinothricin (PPT) sold commercially as Basta, Ignite and Bialophos. The bar gene encodes the enzyme phosphinothricin acetyltransferase, which detoxifies PPT and therefor, should be useful to select the transgenic cells/tissues. The marker gene GUS encodes β-glucuronidase to aid in monitoring DNA delivery into maize tissues for determination of transient and stable expression frequencies. The plasmid pBI101.2 (12.2 kpb; FIG. 3; Clontech) was used as a negative control in bombardment experiments. Plasmid pBI101.2 contained the NPTII coding sequence with the nos promoter and 3' sequences, and the β-glucuronidase coding sequence plus nos 3' without a promoter.

Plasmid DNA Extraction and Purification

The two plasmids (pAHC25, pBI101.2) harbored in separate *Escherichia coli* strains were selectively grown on Luria broth agar medium [10 g/l tryptone (Bacto), 5.0 g/l yeast extract, 5.0 g/l sodium chloride, and 15 g/l Bacto agar, pH 7.5, autoclaved for 35 min. at 121° C., 100 kPa] containing 100 μg/ml ampicillin overnight at 37° C. A single colony was inoculated into 500 ml Luria broth containing 100 μg/ml ampicillin and incubated at 37° C. overnight on a shaker (175 revolutions per min.; rpm). The plasmid DNA was extracted according to the protocol of He et al., 1990. The bacterial culture was first cooled by placing on an ice-bath for 10 min., then transferred into four 250 ml sterile centrifuge bottles and centrifuged at 7000 rpm for 10 min. at 4° C. The supernatant was discarded and 16.7 ml of TELT [2.5 M lithium chloride, 62.5 mM EDTA, pH 8.0, 50 mM Tris base, pH 8.0, 4% (v/v) triton X-100] was added to each bottle. The bacterial cells were re-suspended again by vortexing. An equal volume of phenol:chloroform (1:1; v/v) was added then briefly vortexed. Approximately 5.0 μl (61 mg/ml) of DNase-free RNase was added to each bottle, followed by gentle shaking. Each mixture was incubated at room temperature for 8 min. and centrifuged at 10,000 rpm for 10 min. at 4° C. Each upper aqueous phase was carefully with drawn and transferred to a clean 25 ml sterile Oak Ridge centrifuge tube using pipetmen without disturbing the phases. Approximately two volumes of ice-cold 100% ethanol was added and mixed well to precipitate the plasmid DNA, then centrifuged at 10,000 rpm for 5 min. at room temperature. Supernatants were discarded (completely) and each pellet was washed with 1.0 ml ice-cold 70% ethanol and centrifuged at 10,000 rpm for 5 min. at room temperature. The ethanol was drained off completely by inverting the Oak Ridge tube without disturbing the pellet. Each pellet was dried carefully and dissolved in approximately 1.0 ml TE buffer (10 mM Tris base, 1.0 mM EDTA, pH 8.0) and the concentration of the DNA was checked fluorometrically (Dyna Quant 200; Hoefer). The concentration was adjusted to 1.0 µg/µl in TE buffer, He et al., 1990. For all bombardment experiments, DNA isolated from a single extraction (pAHC25 and pBI101.2) were used.

The isolated plasmid DNA was further purified according to Sambrook et al., 1989. To a known volume of DNA (in TE buffer, pH 8.0), a one-tenth volume of 3.0 M sodium acetate (pH 5.2) and two volumes of 100% ethanol were added, then mixed well by gentle vortexing. The mixture was placed at −20° C. for 20–30 min. and micro-centrifuged (13,000 rpm; all micro-centrifugations were conducted at that speed) for 15 min. The supernatant was discarded and the pellet was dissolved in TE buffer (volume estimated according to the concentration desired) and the volume was adjusted appropriately after quantification fluorometrically to yield plasmid DNA at 1.0 µg/µl.

Sterilization of the Micro-Projectiles

Approximately 60 mg of tungsten micro-projectiles [M10 (0.73 µm) or M25 (1.6 µm)] were weighed and placed in a 1.5 ml micro-centrifuge tube to which 1.0 ml of 100% ethanol was added, then vortexed vigorously for 3 min. The mixture was micro-centrifuged for 1 min. to precipitate the micro-projectiles. The supernatant was discarded and the ethanol wash procedure was repeated twice. The final supernatant was removed and the tungsten micro-projectiles were re-suspended in 1.0 ml 100% ethanol and kept at room temperature overnight. The following day, the mixture was micro-centrifuged for 1 min. The supernatant was discarded and micro-projectiles were washed with 1.0 ml sddw. The tungsten micro-projectiles were then re-suspended in 1.0 ml sterile 50% (v/v) glycerol yielding a 60 mg/ml stock, and stored at −20° C. before use. This procedure of micro-projectile preparation was utilized in all bombardment experiments.

Sterilization of the PDS-1000/He®

The PDS-1000/He® was housed in the laminar air flow hood in 255 Dorman Hall. The interior of the PDS-1000/He® was surface-sterilized by spraying with reagent alcohol (95% ethanol) 30 min. prior to use to allow complete ethanol evaporation. The rupture disk retaining cap, macro-projectile cover lid, macro-projectile holder, macro-projectile launch assembly and target holder were sterilized overnight in the laminar air flow hood by soaking in 100% ethanol (contained in a box) and allowed to dry one hour prior to use in bombardments. The macro-projectiles and rupture disks were also sterilized by soaking in 100% ethanol overnight in a sterile 150 ml beaker and dried in the laminar air flow hood prior to bombardments. The stopping screens were sterilized by autoclaving for 35 min. at 121° C. and 100 KPa pressure. These procedures were followed for all bombardment experiments.

Standard DNA-Tungsten Precipitation and Macro-Projectile Loading

The following describes the standard protocol utilized for DNA-tungsten micro-projectile precipitation and macro-projectile loading, unless noted otherwise. A sterile aliquot of 60 µl tungsten micro-projectiles (M10 or M25; obtained from the 60 mg/ml frozen, sterile stocks) was pipetted into a Treff (Tekmar) micro-centrifuge tube to which 5.0 µl of pAHC25 DNA or pBI101.2 (1.0 µg/µl) was added. Sterile, frozen (−20° C.) 2.5 M CaCl$_2$ solution (50 µl) was added, followed by the addition of 20 µl of sterile frozen (−20° C.) 0.1 M spermidine. This mix was vortexed continuously for 3 min. and then micro-centrifuged for one min. The supernatant was discarded and the micro-projectile-DNA mix was washed with 250 µl 100% ethanol with the supernatant discarded again after micro-centrifugation. The pellet was washed with 70% ethanol and micro-centrifuged as described previously. The micro-projectile-DNA mix was re-suspended in 60 µl 100% ethanol (Bio-Rad instruction manual).

The precipitation and coating of DNA onto micro-projectiles was monitored in initial experiments by staining with 4',6-diamidino-2-phenylindole (DAPI; Sigma). A DAPI stock solution (0.02 mM) was prepared according to Lin et al., 1977, by dissolving in 5.0 mM phosphate buffer (pH 7.5), 1.0 mM EDTA (pH 7.5). Approximately 5.0 µl of the DAPI stock solution was pipetted into a sterile micro-centrifuge tube and 5.0 µl of the DNA-coated tungsten micro-projectiles were also added, then gently vortexed. Approximately 8.0 µl of the stained micro-projectile-DNA mix was placed at the center of a glass slide with a cover-slip and observed for fluorescence under the Olympus BH-2 microscope using the ultra-violet light source. Following confirmation of the presence of pAHC25 or pBI101.2 DNA on the micro-projectiles, the DNA coated micro-projectiles were loaded (12 µl) onto each sterile macro-projectile and dried in the laminar air flow hood. The dried, loaded macro-projectiles were used immediately in bombardments of the four target tissues.

Pressure

Three different helium pressures were tested to determine the optimal pressure for DNA delivery into all four target tissue excised from the four genotypes listed previously. The plasmid DNA (pAHC25 and pBI101.2; 1.0 µg/µl) were precipitated separately onto M-25 (1.6 µm) tungsten micro-projectiles using 2.5 M CaCl$_2$. The bombardments were performed utilizing the three pressures with 1.0 cm gap and 7.5 cm target distances for all target tissues. Approximately 1.0 µg DNA and 720 µg tungsten micro-projectiles were delivered per shot. The critical pressure was first determined which was the pressure at which the target tissues were drastically affected (damaged) by the blast impact. Once the critical pressure was known, then pressure levels less than the critical value were tested. A pressure of 1100 psi was determined critical for all the tissues. Therefor, the three helium pressures tested in optimization experiments were 450, 650 and 900 psi. The optimal pressure was determined via transient GUS assays conducted three days post-bombardment.

Tungsten Micro-Projectile Size

Two tungsten micro-projectile sizes, M-10 (0.73 µm) and M-25 (1.6 µm) were compared in transient GUS assays (three days post-bombardment) to determine the ideal tungsten micro-projectile size for all four target tissues obtained from the four initial genotypes. Standard DNA-tungsten precipitation was utilized and bombardments were conducted at 650 psi helium pressure with 1.0 cm gap and 7.5 cm target distances. Once the optimal tungsten micro-projectile size was determined, the effects of using freshly prepared versus frozen tungsten M-25 (0.16 µm) micro-projectiles were also evaluated following bombardments and screening of the four target tissues from the four genotypes via transient GUS assays. The bombardments were conducted as previously noted and approximately 1.0 µg of DNA and 720 µg of tungsten micro-projectiles were delivered per shot.

Optimal DNA and CaCl$_2$ Concentrations for Precipitation onto the Micro-Projectiles Two additional DNA (2.0 and 3.0 µg/µl) concentrations were compared with the standard concentration of 1.0 µg/µl for all the target tissue types as evaluated in transient GUS assays conducted three days post bombardment. The standard DNA-micro-projectile (M-25) precipitations (2.5 M CaCl$_2$) were followed which resulted in 2.0 µg and 3.0 µg DNA delivered per shot, respectively (versus the standard 1.0 µg/shot) along with 720 µg tungsten per shot. Independent of this, three different $CaCl_2$ concentrations (0.5, 1.0 and 1.5 M) were compared with the standard 2.5 M concentration for DNA (1.0 μg/μl) precipitation, testing all four target tissues derived from four genotypes in transient GUS assays conducted three days post-bombardment. DNA precipitations were conducted separately utilizing different concentrations of $CaCl_2$ with M-25 micro-projectiles. Approximately 1.0 μg of DNA and 720 μg of tungsten micro-projectiles were delivered per shot. For all, bombardments utilized a helium pressure of 650 psi with 1.0 cm gap and 7.5 cm target distances.

Amount of DNA-Micro-Projectile Mix Loaded and Delivered Per Shot

Three different amounts (1.0 μl, 5.0 μl, and standard 12 μl) of DNA-tungsten (M-25) micro-projectiles were loaded onto macro-projectiles. This resulted in 60, 300 and 720 μg tungsten with 0.08, 0.42, and 1.0 μg DNA delivered per shot, respectively. Standard DNA (1.0 μg/μl) precipitation (2.5 M $CaCl_2$) was conducted with M-25 tungsten micro-projectiles. Bombardments were conducted at 650 psi helium pressure with 1.0 cm gap and 7.5 cm target distances for all four target tissue types obtained from the four initial genotypes. Optimal quantity of tungsten micro-projectiles delivered per shot were evaluated in transient GUS assays conducted three days post-bombardment.

Testing Gap Distances

Three different gap distances were compared: 0.32, 0.65 and 1.0 cm. Standard DNA (1.0 μg/μl) precipitation onto M-25 tungsten micro-projectiles was conducted using 2.5 M $CaCl_2$. The bombardments utilized 650 psi helium pressure and a 7.5 cm target distance testing all target tissues obtained from the four initial genotypes. Approximately 0.96 μg of DNA and 720 μg of tungsten micro-projectiles were delivered per shot. Optimal gap distance was determined based on transient GUS assays conducted three days post-bombardment.

Testing Optimal Plating Density

The number of target tissues placed at the central 2.5 cm target area (diameter) of the petri plate were compared with the standard number listed first: 30 vs 35 immature zygotic embryos, 24 vs 30 mature zygotic embryos, and 40 vs 50 nodal sections (each source). Standard DNA (1.0 μg/μl) precipitation onto M-25 tungsten micro-projectiles was conducted with 2.5 M $CaCl_2$. The bombardments were conducted at 650 psi helium pressure with 1.0 cm gap and 7.5 cm target distances for three tissues: nodal sections excised from germinated immature embryos, immature zygotic embryos and mature zygotic embryos. A gap distance of 0.65 cm (with identical helium pressure and target distance) were used for bombardment of nodal sections excised from mature seedlings. Approximately 1.0 μg of DNA and 720 μg of tungsten micro-projectiles were delivered per shot. All four genotypes were screened and assayed for GUS expression three days post-bombardment.

Results for Regeneration

Immature zygotic embryos (14 dpp) from four genotypes, (commercial hybrids: Dekalb 683, Pioneer 3085, Pioneer 3156, and inbreds: Sc229-1 and Sc229-2) were placed on three MS-based media supplemented with 1.0 mg/l kinetin and sucrose (w/v basis) at 12% (Medium $M_1$), 15% (medium $M_2$), or 17% (medium $M_3$). Cultures were incubated in the dark at room temperature to determine the ideal medium which allowed maturation of immature zygotic embryos and prevented precocious germination.

Immature zygotic embryos were creamish-white in color and approximately 1.5 mm in length prior to being placed on maturation media. Embryos began to swell and increased in size within four days on all maturation media. The creamish-white zygotic embryos (at the center of the scutella) gradually became dense white in color and looked similar to mature zygotic embryos within five days after culture initiation. At that time, plates were transferred to a 16 h photoperiod. After approximately three additional days, the coleoptile and coleorhiza became visible and embryos germinated to give rise to normal seedlings. However, seedlings were smaller in size compared to those that arose from mature seeds.

All three media were effective on all genotypes and promoted maturation within seven days from culture initiation. Looking at calculated averages for the four genotypes within individual media, immature zygotic embryos on medium $M_2$ and $M_3$ yielded comparable responses (96% and 95%, respectively) and appeared to perform better than $M_1$ (87%; Table 13). Within individual genotypes, results were not as clear. That is why the averages were used as a basis to select the medium to use in additional screenings. Since media $M_2$ and $M_3$ were comparable, $M_2$ was chosen because Lowe et al., 1995, obtained similar maturation responses on a MS-based medium supplemented with the same percentage sucrose (plus 1.0 mg/l zeatin and 1.0 mg/l IAA).

Screening for Genotype-Independence of Immature Zygotic Embryo Maturation Protocol Following pre-screening with the four genotypes, immature embryos from all 21 genotypes were evaluated on medium $M_2$. Maturation responses after seven days in culture for all genotypes ranged from 93–98%, with a calculated average of 96% (Table 14). No genotypic differences could be detected with inbred immature zygotic embryos responding as well as those of commercial hybrid genotypes.

TABLE 13

Percentages of immature zygotic embryos (14 dpp) from four maize genotypes capable of maturation on three sucrose-rich media[z] after seven days in culture.

| | Percent Maturation | | |
|---|---|---|---|
| Genotype | $M_1$ | $M_2$ | $M_3$ |
| Dekalb 683 | 84 ± 11 | 98 ± 3.0 | 96 ± 3.0 |
| Pioneer 3085 | 89 ± 3.0 | 96 ± 3.0 | 96 ± 3.0 |
| Pioneer 3156 | 91 ± 8.0 | 98 ± 3.0 | 98 ± 3.0 |
| Sc229-1 | 84 ± 11 | 96 ± 3.0 | 93 ± 3.0 |
| Sc229-2 | 87 ± 14 | 93 ± 5.0 | 91 ± 6.0 |
| Avg.[y] | 87 ± 3.0 | 96 ± 3.0 | 95 ± 2.0 |

Numbers represent mean percent response ± standard deviation from 15 embryos per plate with 3 replicate plates (rounded to the nearest whole number)
[z]MS-based medium each containing 12% ($M_1$), 15% ($M_2$) and 17% (w/v; $M_3$) sucrose plus 1.0 mg/l kinetin
[y]Average calculated value ± standard deviation among those numbers within each medium

TABLE 14

Percentages of immature zygotic embryos (12–14 dpp) capable of maturation from 21 maize genotypes on medium $M_2$[z] after seven days in culture.

| | Genotype | Percent Maturation |
|---|---|---|
| Grain hybrids | Agratech 810 | 96 ± 3.0 |
| | Agratech 888$F_4$ | 96 ± 3.0 |
| | Asgrow Rx897 | 98 ± 3.0 |
| | Asgrow Rx899 | 98 ± 3.0 |
| | Cargill X9255 | 96 ± 3.0 |
| | Cargill 8327 | 98 ± 3.0 |
| | Dekalb 649 | 98 ± 3.0 |
| | Dekalb 683 | 98 ± 3.0 |
| | ICI 8281 | 96 ± 3.0 |
| | Northnip King n7787 | 96 ± 3.0 |
| | Northnip King n8811 | 96 ± 3.0 |

TABLE 14-continued

Percentages of immature zygotic embryos (12–14 dpp) capable of maturation from 21 maize genotypes on medium $M_2{}^z$ after seven days in culture.

|  | Genotype | Percent Maturation |
|---|---|---|
|  | Pioneer 3085 | 96 ± 3.0 |
|  | Pioneer 3145 | 98 ± 3.0 |
|  | Pioneer 3156 | 96 ± 3.0 |
|  | Pioneer 3167 | 93 ± 5.0 |
|  | TR 1185 | 96 ± 3.0 |
| Sweet corn hybrid | Funks G90 | 96 ± 3.0 |
| Inbreds | Mp708 | 96 ± 3.0 |
|  | Sc229-1 | 93 ± 5.0 |
|  | Sc229-2 | 96 ± 3.0 |
|  | Tx601 | 96 ± 3.0 |
|  | Va35 | 96 ± 3.0 |
| Avg.$^y$ |  | 96 ± 1.0 |

Numbers represent mean percent response ± standard deviation from 15 embryos per plate with 3 replicate plates (rounded to the nearest whole number)
$^z$MS-based medium each containing 12%(w/v) sucrose plus 1.0 mg/l kinetin
$^y$Average calculated value ± standard deviation among those numbers for all 21 genotypes Adventitious Shoot Organogenesis from Seedling Nodal Section Explants Nodal section explants were excised from five day old germinated embryos (immature; post-maturation) and seedlings (mature seeds) of four genotypes and placed on six MS-based media (A–F) which were supplemented with 2.0 mg/l BAP plus different concentrations (0.25–0.75 mg/l) of CPA or 2,4-D. Explants were cultured under a 16 h photoperiod and numbers of adventitious shoots were counted eight weeks after initiation.

Regardless of origin, nodal sections excised from all four genotypes elongated slightly and initiated multiple micro-shoots on four of the six media [contained 0.25 or 0.5 mg/l CPA (A,B) or 2,4-D (D, E)] within 8–10 days and were visible under a binocular dissecting microscope. Although the shoot apical meristem had been discarded, it appeared that adventitious shoots were produced by rapid and direct proliferation of one (or more) preformed shoot meristem located within the explant, without callus production. Micro-shoots developed in clusters all over the upper surface of each nodal section regardless of source in all four genotypes. Developing leaves from micro-shoots appeared normal (sometimes curled) and possessed trichomes which covered the mini-leaf blades visible under a binocular dissecting microscope. Wernicke and Milkovits, 1986, determined that 2,4-D promoted proliferation of immature *Triticum aestivum* L. (wheat) shoot meristem(s) within the node. They suggested that this occurred by suppression of the pre-formed and newly arisen meristems. It was also proposed that 2,4-D retained those meristems in a budding (continuous proliferation) state and this kind of response was a common feature of cereal cell cultures, Wernicke and Milkovits, 1986. Similar to this, Raman et al., 1980, observed in their maize shoot tip cultures, that the shoot apical meristems formed multiple shoots on a MS-based medium supplemented with adenine sulfate dihydrate (120 mg/l), kinetin (3.0 mg/l) plus IAA or IBA (1.0 mg/l). In our preliminary experiments, we observed that 2,4-D and CPA could induce adventitious multiple shoot proliferation on two sources of nodal section explants.

Table 15 summarizes the average number of adventitious shoots produced per nodal section explant for each genotype on the six media. Results demonstrated that nodal sections excised from both sources could successfully produce shoots. With very few individual exceptions, media A (0.25 mg/l CPA plus 2.0 mg/l BAP) and D (0.25 g/l 2,4-D plus 2.0 mg/l BAP) generated greater numbers of shoots on both sources of nodal section explants within and among genotypes (Table 15). Among genotypes, medium A (versus D) yielded similar or greater combined calculated averages for both nodal section types. The same trend was noted within individual genotypes (Table 15). The only noted difference between explant sources was also observed in medium A, where greater numbers of shoots (per individual genotype and combined average) were produced on nodal sections excised from immature germinated embryos. (Within D, only one individual genotypic difference was noted between the two explant sources, but the combined calculated averages were similar).

Multiple-shoot cultures subcultured after four weeks onto the same initial media increased in number. Micro-shoots, separated at the end of eight weeks, elongated after transfer onto a PGR-free basal MS medium (supplemented with 10 mg/l glycine and 150 mg/l asparagine) within three weeks when cultured under a 16 h photoperiod. Individual shoots increased in size by expansion of leaf blades coupled with internodal elongation. Elongated shoots rooted successfully within three weeks after transfer onto the same basal medium supplemented with 0.5 mg/l IBA (MSR) and produced intact plantlets. Two plantlets regenerated from each of the four genotypes were transplanted to a soilless mix in pots and acclimatized, then transplanted to soil and grown to maturity in the greenhouse. No phenotypic abnormalities were noted for the regenerated plants from all four genotypes.

TABLE 15

Adventitious shoot regeneration from nodal sections excised from germinated immature embryos and seedlings on six different media for four maize genotypes after eight weeks in culture.

| Genotype | Media$^z$ | | | | | |
|---|---|---|---|---|---|---|
|  | A | B | C | D | E | F |

No. Shoots per nodal section (immature germinated embryo)

| | | | | | | |
|---|---|---|---|---|---|---|
| Dekalb 683 | 47.3 ± 6.0 | 19.1 ± 5.1 | 12.4 ± 2.3 | 20.1 ± 2.1 | 16.3 ± 3.6 | 11.6 ± 2.2 |
| Pioneer 3085 | 43.1 ± 3.6 | 14.1 ± 4.8 | 15.3 ± 1.2 | 26.2 ± 2.9 | 24.8 ± 2.4 | 16.7 ± 2.8 |
| Pioneer 3156 | 46.7 ± 4.8 | 15.2 ± 2.4 | 14.1 ± 1.2 | 45.3 ± 4.9 | 13.4 ± 1.8 | 12.3 ± 1.4 |

TABLE 15-continued

Adventitious shoot regeneration from nodal sections excised from
germinated immature embryos and seedlings on six different media
for four maize genotypes after eight weeks in culture.

| | Genotype | Media[2] | | | | | |
|---|---|---|---|---|---|---|---|
| | | A | B | C | D | E | F |
| | Sc229-1 | 41.9 ± 3.2 | 16.3 ± 2.6 | 15.9 ± 2.4 | 31.9 ± 2.4 | 17.9 ± 2.1 | 10.1 ± 1.6 |
| | Sc229-2 | 44.6 ± 3.6 | 17.1 ± 1.2 | 15.3 ± 3.2 | 31.1 ± 3.1 | 16.9 ± 1.2 | 12.7 ± 2.4 |
| Avg.[y] | | 44.7 ± 2.0 | 16.3 ± 1.7 | 14.6 ± 1.2 | 30.9 ± 8.3 | 17.8 ± 3.8 | 12.7 ± 2.1 |
| | | No. Shoots per nodal section (seedling) | | | | | |
| | Dekalb 683 | 36.1 ± 2.4 | 14.2 ± 2.1 | 10.2 ± 1.2 | 16.1 ± 1.9 | 23.4 ± 2.5 | 10.1 ± 2.2 |
| | Pioneer 3085 | 35.3 ± 2.3 | 11.3 ± 1.9 | 16.4 ± 2.3 | 23.5 ± 2.4 | 24.6 ± 2.8 | 9.3 ± 1.7 |
| | Pioneer 3156 | 32.2 ± 2.1 | 10.2 ± 1.4 | 13.2 ± 2.1 | 32.6 ± 1.3 | 23.1 ± 2.5 | 11.2 ± 2.1 |
| | Sc229-1 | 29.1 ± 1.2 | 15.6 ± 2.5 | 10.7 ± 1.6 | 27.3 ± 3.3 | 13.9 ± 1.3 | 8.7 ± 2.2 |
| | Sc229-2 | 36.4 ± 2.5 | 13.2 ± 2.3 | 13.6 ± 1.9 | 29.8 ± 3.8 | 18.2 ± 2.4 | 4.2 ± 0.9 |
| Avg. | | 33.8 ± 2.8 | 12.9 ± 1.9 | 12.8 ± 2.2 | 25.9 ± 5.7 | 20.6 ± 4.0 | 8.7 ± 2.4 |

Number represent mean ± standard deviation of three replicate with 5 explants per replicate plate
[z]MS-based media containing 3% (w/v) sucrose and 2.0 mg/l BAP; A–C contains 0.25, 0.5, 0.75 mg/l CPA respectively; D–F contains 0.25, 0.5, 0.75 mg/l 2,4-D, respectively
[y]Average calculated value ± standard deviation among those numbers within each medium Screening for Genotype-Independence of the Organogenic Regeneration Protocol Following pre-screening, two media (A and D) were chosen to evaluate nodal section (two sources) responses for the 21 genotypes. Adventitious shoots formed on both sources of nodal sections from both maturity types and followed a similar trend as described previously for pre-screened genotypes (Table 15, 16). Nodal sections placed on medium A yielded comparable or greater numbers of shoots within and among all genotypes regardless of explant source (Table 16). Within medium A, immature nodal sections (excised from germinated immature embryos) gave greater responses than their seedling counterparts within and among all genotypes. Within medium D, comparison of the combined averages determined that both sources of nodal sections yielded similar numbers of adventitious shoots and were similar to mature explants on medium A (Table 16). It was evident that explant source and medium both contributed to the number of shoots generated per explant.

With this developed regeneration system, the numbers of shoots obtained from nodal section explants rivaled the numbers reported to be generated from pre-formed shoot tips. Zhong et al., 1992, produced multiple shoot clumps (20–50 shoots per explant) from shoot tips excised from germinated seedlings (mature seeds) for 21 maize genotypes (no quantitative data given for all 21 genotypes) on a MS-based medium supplemented with BAP, (2.0 mg/l) and 500 mg/l casein hydrolysate, and cultured in the dark. In Honey N Pearl, precociously germinated immature embryo seedling shoot tips placed on a medium supplemented with 2,4-D (0.5 mg/l) and BAP (2.0 mg/l) yielded approximately 10 shoots per explant, Zhong et al., 1992.

Adventitious shoots from all 21 genotypes were excised following eight weeks of culture, elongated on medium MS-0 (supplemented with 10 mg/l glycine and 150 mg/l asparagine) for three weeks and, then placed on a rooting medium (MSR, MS-based medium containing 0.5 mg/l IBA; 3 weeks) to form plantlets. Elongation and rooting were successful in all 21 genotypes. Two plantlets per genotype were acclimatized and successfully transplanted to soil in pots, but the plants were lost due to lack of care, and therefor, not grown to maturity.

Adventitious shoot regeneration was demonstrated in all 21 genotypes which included both inbreds and commercial hybrids. Therefor, the regeneration protocols were determined to be genotype-independent, although differences between genotypes in regard to degrees of response were noted. Regardless, both explant sources responded to produce multiple adventitious shoots capable of forming plantlets in approximately 14 weeks. When compared to results obtained in Experiment I, greater numbers of shoots could be produced per nodal section explant, regardless of source (maturity). Maize regeneration via nodal section explants is unique and could be coupled with biolistic transformation protocols. If amenable to DNA uptake, such genotype-independent regeneration protocols could find potential use in developing more efficient maize transformation systems.

TABLE 16

Adventitious shoot regeneration from nodal sections excised from germinated
immature embryos and seedlings from 21 maize genotypes on media A and D after
eight weeks in culture.

| | | No. Shoots Per Nodal Section | | | |
|---|---|---|---|---|---|
| | | Immature Germinated Embryo | | Seedling | |
| | Genotype | A | D | A | D |
| Grain Hybrids | Agratech 810 | 42.5 ± 3.2 | 13.4 ± 1.3 | 34.2 ± 3.5 | 22.5 ± 2.5 |
| | Agratech 888F[4] | 43.9 ± 2.9 | 21.2 ± 2.6 | 33.6 ± 3.4 | 17.2 ± 2.3 |
| | Asgrow Rx897 | 45.3 ± 3.7 | 20.9 ± 1.9 | 29.3 ± 2.4 | 23.7 ± 2.6 |
| | Asgrow Rx899 | 52.4 ± 7.1 | 30.1 ± 3.4 | 36.2 ± 2.9 | 32.1 ± 4.0 |

TABLE 16-continued

Adventitious shoot regeneration from nodal sections excised from germinated immature embryos and seedlings from 21 maize genotypes on media A and D after eight weeks in culture.

|  | | No. Shoots Per Nodal Section | | | |
|---|---|---|---|---|---|
|  | | Immature Germinated Embryo | | Seedling | |
|  | Genotype | A | D | A | D |
|  | Cargill X9255 | 44.7 ± 3.8 | 36.1 ± 3.6 | 34.1 ± 3.7 | 27.2 ± 3.3 |
|  | Cargill 8327 | 41.2 ± 2.5 | 34.2 ± 2.9 | 29.8 ± 3.3 | 26.6 ± 3.2 |
|  | Dekalb 649 | 52.2 ± 6.8 | 19.4 ± 2.2 | 37.1 ± 3.2 | 22.3 ± 2.6 |
|  | Dekalb 683 | 49.0 ± 4.2 | 21.6 ± 2.5 | 33.7 ± 3.4 | 19.7 ± 2.1 |
|  | ICI 8281 | 46.8 ± 3.4 | 22.5 ± 2.2 | 35.2 ± 3.7 | 21.9 ± 2.7 |
|  | Northrup King n7787 | 41.2 ± 2.5 | 32.1 ± 3.4 | 28.3 ± 2.6 | 23.1 ± 2.4 |
|  | Northrup King n8811 | 40.6 ± 1.7 | 36.2 ± 3.8 | 29.4 ± 2.4 | 19.4 ± 2.2 |
|  | Pioneer 3085 | 43.6 ± 2.1 | 29.3 ± 2.9 | 35.2 ± 3.7 | 16.1 ± 1.8 |
|  | Pioneer 3145 | 47.8 ± 3.4 | 33.9 ± 3.2 | 33.9 ± 3.4 | 29.7 ± 3.8 |
|  | Pioneer 3156 | 48.6 ± 2.9 | 27.7 ± 3.1 | 33.1 ± 3.3 | 25.8 ± 3.1 |
|  | Pioneer 3167 | 46.2 ± 3.5 | 32.2 ± 3.2 | 34.5 ± 2.5 | 22.4 ± 2.6 |
|  | TR 1185 | 56.1 ± 7.6 | 12.2 ± 1.2 | 24.3 ± 1.4 | 21.3 ± 2.4 |
| Sweet corn hybrid | Funks G90 | 47.2 ± 2.8 | 33.4 ± 4.1 | 31.2 ± 3.3 | 24.1 ± 2.7 |
| Inbreds | Mp708 | 37.6 ± 2.5 | 29.2 ± 2.2 | 29.7 ± 3.3 | 23.2 ± 2.4 |
|  | Sc229-1 | 42.1 ± 3.3 | 33.1 ± 3.1 | 28.3 ± 2.6 | 28.6 ± 2.6 |
|  | Sc229-2 | 46.9 ± 3.4 | 32.8 ± 3.4 | 30.1 ± 3.3 | 31.4 ± 3.2 |
|  | Tx601 | 38.4 ± 3.3 | 28.6 ± 2.9 | 28.2 ± 2.6 | 30.2 ± 2.9 |
|  | Va35 | 43.3 ± 2.7 | 34.6 ± 4.2 | 26.7 ± 1.9 | 29.1 ± 2.7 |
| Avg.[y] | | 45.4 ± 4.4 | 27.9 ± 6.9 | 31.6 ± 3.3 | 24.4 ± 4.4 |

Numbers represent mean ± standard deviation of the mean of three replicate plates with 5 explants per replicate
[y]Average calculated value ± standard deviation among those numbers for all 21 genotypes within each medium Results—Biolistic Transformation Large scale plasmid DNA (pAHC25 and pBI101.2) extractions were conducted following modification of a lithium mini-prep protocol, He et al., 1990. Plasmid DNA yields of 5.0–6.0 mg per 500 ml culture were obtained. Plasmid pAHC25 served as the primary source of foreign DNA. As detailed previously, it contained GUS as the reporter gene and bar as the selectable marker gene, while the negative control, pBI101.2, contained a GUS coding sequence that lacked a promoter. For all bombardment experiments, plasmid DNA (pAHC25 and pBI101.2) isolated from a single extraction were utilized in the following experiments to preclude DNA variability between experiments. DNA was purified and concentrated to remove phenol contamination during extraction, with concentrations adjusted to 1.0 μg/μl in TE buffer, pH 8.0 and confirmed fluorometrically.

Optimization of Bombardment Protocols

Nodal sections excised from immature germinated embryos and mature seedlings were utilized as targets for foreign DNA uptake. Optimized gene delivery for all types via PDS-100/He® was determined via transient GUS assays, conducted three days post-bombardment. Initially, foreign DNA delivery was optimized for eight biolistic-related parameters for each explant source harvested from the four genotypes consistently used in pre-screenings (Dekalb 683, Pioneer 3085, Pioneer 3156, Sc229-1 and Sc229-2). Optimized protocols were then used to target the four explant sources from all 21 genotypes to determine genotype-independence of the protocols. A pre-set target distance of 7.5 cm was used for all bombardments. Initial experiments determined that target distances less 7.5 cm caused severe visible damage to all four target tissue types and sometimes the target explants were blown from the plate.

Determination of Optimal Helium Pressure (Rupture Disk Strength)

Rupture disks that burst at three different helium pressures (450, 650 and 900 psi) were used for the bombardments of standard numbers of immature and mature seedling nodal sections (40 per plate), and immature (30 per plate) and mature (24 per plate) zygotic embryos from the four genotypes. Target tissues were bombarded independently with pAHC25 (3 replicate plates) and pBI101.2 (2 replicate plates) DNA for each tested variable in this and all subsequent experiments. Unless noted, all bombardments utilized a standard DNA precipitation protocol according to Bio-Rad (Bio-Rad instruction manual; 2.5 M $CaCl_2$). In this experiment, DNA (1.0 μg/shot) coated onto 1.6 μm tungsten micro-projectiles (720 μg tungsten/shot), and a gap distance of 1.0 cm were utilized.

Results determined that all target tissues from five genotypes bombarded at 650 psi displayed greater numbers of GUS-positive sectors (blue spots) within and among genotypes (two exceptions: Pioneer 3156 IS, Sc-229-2 immature embryos), identified in transient assays (Table 18). Bombardments at 650 psi could yield approximately twice the number of blue sectors versus 450 and 900 psi, which yielded comparable numbers. Within three of the four individual explant sources bombarded at 650 psi, some differences between genotypes were noted (Table 18). In IS, Pioneer 3085 and Sc229-2 yielded greater numbers of GUS-positive sectors than Dekalb 683 and Pioneer 3156. Dekalb 683 immature zygotic embryos performed better than Pioneer 3156 and Sc229-2, with Pioneer 3086 mature zygotic embryos outperforming Dekalb 683, Sc-229-1 and Sc229-2. However, since all genotypes were capable of DNA uptake in all each explant source, all were classified as genotype-independent DNA introduction protocols which would be further optimized in the following sections.

As expected, mean numbers of blue spots per explant differed between explant tissues, and appeared to correlate to target surfaces of each explant type. The larger the target surface area, the greater numbers of GUS-positive sectors.

Target tissues bombarded with pBI101.2 (negative control plasmid DNA) did not yield any GUS-positive sectors in this, or any other optimization experiment. With the results described above, it was determined that a helium pressure of 650 psi was ideal for bombardment of each of the target tissue types.

TABLE 18

Evaluation of optimal helium pressure (rupture disk strength) determined in transient GUS assays three days post-bombardment on nodal sections excised from germinated immature embryos (IS) and mature (MS) seedlings, and immature and mature zygotic embryos from four maize genotypes.

| | Helium Pressure/Rupture Disk Strength (psi) | | |
|---|---|---|---|
| | 450 | 650 | 990 |
| Genotype | No. GUS positive sectors/explant | | |
| Nodal sections (IS) | | | |
| Dekalb 683 | 1.4 ± 0.4 | 2.3 ± 0.3 | 1.2 ± 0.4 |
| Pioneer 3085 | 1.3 ± 0.4 | 3.3 ± 0.4 | 1.3 ± 0.4 |
| Pioneer 3156 | 1.2 ± 0.4 | 2.1 ± 0.5 | 1.4 ± 0.4 |
| Sc229-1 | 1.4 + 0.4 | 2.6 ± 0.7 | 1.2 ± 0.4 |
| Sc229-2 | 1.8 ± 0.6 | 3.1 ± 0.4 | 2.0 ± 0.3 |
| Avg.[z] | 1.4 ± 0.2 | 2.7 ± 0.4 | 1.4 ± 0.2 |
| Nodal sections (MS) | | | |
| Dekalb 683 | 1.1 ± 0.3 | 3.2 ± 0.4 | 1.2 ± 0.4 |
| Pioneer 3085 | 1.6 ± 0.4 | 2.9 ± 0.4 | 1.4 ± 0.4 |
| Pioneer 3156 | 1.3 ± 0.4 | 3.3 ± 0.4 | 1.8 ± 0.4 |
| Sc229-1 | 1.2 ± 0.4 | 3.1 ± 0.3 | 1.1 ± 0.3 |
| Sc229-2 | 1.7 ± 0.4 | 2.9 ± 0.3 | 1.3 ± 0.4 |
| Avg. | 1.4 ± 0.2 | 3.1 ± 0.1 | 1.4 ± 0.2 |
| Immature zygotic embryos | | | |
| Dekalb 683 | 2.1 ± 0.5 | 4.3 ± 0.4 | 1.3 ± 0.4 |
| Pioneer 3085 | 1.8 ± 0.5 | 4.0 ± 0.4 | 1.6 ± 0.4 |
| Pioneer 3156 | 1.4 ± 0.4 | 3.3 ± 0.4 | 1.9 ± 0.6 |
| Sc229-1 | 1.5 ± 0.4 | 4.0 ± 0.6 | 1.2 ± 0.4 |
| Sc229-2 | 1.9 ± 0.6 | 2.8 ± 0.8 | 2.1 ± 0.4 |
| Avg. | 1.7 ± 0.2 | 3.7 ± 0.5 | 1.6 ± 0.3 |
| Mature zygotic embryos | | | |
| Dekalb 683 | 4.9 ± 0.5 | 10.1 ± 0.7 | 4.7 ± 0.4 |
| Pioneer 3085 | 6.3 ± 0.4 | 11.9 ± 0.7 | 5.6 ± 0.6 |
| Pioneer 3156 | 5.2 ± 0.6 | 10.2 ± 1.1 | 4.3 ± 0.4 |
| Sc229-1 | 4.8 ± 0.7 | 9.8 ± 1.0 | 3.9 ± 0.5 |
| Sc229-2 | 5.9 ± 0.6 | 9.6 ± 1.0 | 5.1 ± 0.7 |
| Avg. | 5.4 ± 0.5 | 10.3 ± 0.8 | 4.7 ± 0.5 |

Number represent mean number of GUS-positive sectors (blue spots) ± standard deviation of three random samples taken per plate bombarded with pAHC25, with 3 replicate plates sampled
[z]Average calculated value ± standard deviation among those numbers within each helium pressure/rupture disk strength Determination of Optimal Tungsten Micro-Projectile Size To determine the optimal tungsten micro-projectile size for each of the tissue types in all four genotypes, two tungsten sizes, 0.73 μm and 1.6 μm, were compared. The bombardments utilized the standard DNA precipitation protocol, 730 μg tungsten and 1.0 μg DNA per shot, helium pressure (650 psi) and gap distance (1.0 cm). The same numbers of targets and replicates per explant type were used in this and subsequent experiments as described int he previous section. Results determined that all target tissues bombarded with 1.6 μm tungsten micro-projectiles could yield nearly almost twice the numbers of GUS positive sectors compared to 0.73 μm in all five genotypes (Table 19).

TABLE 19

Evaluation of optimal tungsten size determined in transient GUS assays three days post-bombardment on nodal sections excised from germinated immature embryos (IS) and mature (MS) seedlings, and immature and mature zygotic embryos from four maize genotype.

| | Tungsten size (μm) | |
|---|---|---|
| | 0.73 | 1.6 |
| Genotype | No. GUS positive sectors/explant | |
| Nodal sections (IS) | | |
| Dekalb 683 | 1.3 ± 0.4 | 3.6 ± 0.5 |
| Pioneer 3085 | 1.5 ± 0.4 | 3.9 ± 0.5 |
| Pioneer 3156 | 1.3 ± 0.4 | 3.2 ± 0.4 |
| Sc229-1 | 1.3 + 0.4 | 3.1 ± 0.3 |
| Sc229-2 | 1.4 ± 0.4 | 3.1 ± 0.4 |
| Avg.[z] | 1.4 ± 0.1 | 3.4 ± 0.3 |
| Nodal sections (MS) | | |
| Dekalb 683 | 1.3 ± 0.4 | 3.6 ± 0.5 |
| Pioneer 3085 | 2.2 ± 0.4 | 3.2 ± 0.4 |
| Pioneer 3156 | 1.1 ± 0.3 | 3.6 ± 0.4 |
| Sc229-1 | 2.1 ± 0.5 | 3.1 ± 0.4 |
| Sc229-2 | 1.6 ± 0.4 | 2.9 ± 0.3 |
| Avg. | 1.7 ± 0.4 | 3.3 ± 0.3 |
| Immature zygotic embryos | | |
| Dekalb 683 | 1.6 ± 0.4 | 4.6 ± 0.5 |
| Pioneer 3085 | 1.4 ± 0.4 | 3.4 ± 0.5 |
| Pioneer 3156 | 1.2 ± 0.4 | 3.2 ± 0.4 |
| Sc229-1 | 2.4 ± 0.6 | 4.4 ± 0.5 |
| Sc229-2 | 2.6 ± 0.5 | 3.2 ± 0.4 |
| Avg. | 1.8 ± 0.5 | 3.7 ± 0.6 |
| Mature zygotic embryos | | |
| Dekalb 683 | 4.4 ± 0.5 | 10.1 ± 0.7 |
| Pioneer 3085 | 5.6 ± 0.6 | 10.4 ± 0.7 |
| Pioneer 3156 | 4.3 ± 0.4 | 10.6 ± 0.7 |
| Sc229-1 | 4.7 ± 0.4 | 10.3 ± 0.8 |
| Sc229-2 | 3.8 ± 0.6 | 9.7 ± 0.5 |
| Avg. | 4.7 ± 0.6 | 10.2 ± 0.3 |

Number represent mean number of GUS-positive sectors (blue spots) ± standard deviation of three random samples taken per plate bombarded with pAHC25, with 3 replicate plates sampled
[z]Average calculated value ± standard deviation among those numbers within each tungsten size Independent of the above experiment, frozen tungsten micro-projectiles (1.6 μm) used for bombardment at 650 psi yielded greater numbers of GUS-positive sectors on all four target tissues within and among genotypes [exception: Pioneer 3156 (IS) and Sc229-2 (immature zygotic embryos)] compared to micro-projectiles prepared fresh (Table 20). (Frozen micro-projectiles were prepared days to months in advance and stored in the freezer until the day of bombardment). Within individual explant sources bombarded with frozen 1.6 μm tungsten micro-projectiles, some differences were noted between the genotypes. In IS, three genotypes (Dekalb 683, Sc229-1 and Sc229-2) yielded greater numbers of GUS-positive sectors than Pioneer 3156. Immature zygotic embryos from Dekalb 683, Pioneer 3085 and Sc229-1 performed better than Sc229-2. Mature zygotic embryos from Dekalb 683 displayed greater numbers of GUS-positive sectors compared to Pioneer 3156, Sc229-1 and Sc229-2. Regardless of slight genotypic differences, these results indicated that tungsten micro-projectiles stocks could be frozen in 50% glycerol until use. The extended contact period between tungsten micro-projectiles and 50% glycerol (along with possible freeze-related changes) may have contributed to greater numbers of GUS-positive sectors compared to the fresh stocks. Ratnayaka and Oard, 1995, observed higher GUS expression with bombarded non-regenerable rice suspension cells when 100 μl of 50% glycerol was incorporated during precipitation of DNA onto tungsten micro-projectiles (frozen or fresh; 0.2–1.5 µm). It was deduced that maintaining tungsten-micro-projectile stocks in 50% glycerol was advantageous and aided in higher transient GUS expression.

With results described above, it was determined that 1.6 µm frozen tungsten micro-projectiles were ideal for bombardments at 650 psi for all maize target explants. In addition, it was apparent that the pre-set target distance (7.5 cm) and a gap distance (1.0 cm) did not preclude DNA introduction.

TABLE 20

Evaluation of fresh versus frozen 1.6 µm tungsten micro-projectiles via transient GUS assays three days post-bombardment on nodal sections excised from germinated immature embryos (IS) and mature (MS) seedlings, and immature and mature zygotic embryos from four maize genotypes.

| | Tungsten size (1.6 µm) | |
|---|---|---|
| | Fresh | Frozen |
| Genotype | No. GUS positive sectors/explant | |
| Nodal sections (IS) | | |
| Dekalb 683 | 1.4 ± 0.4 | 3.6 ± 0.5 |
| Pioneer 3085 | 1.2 ± 0.4 | 3.3 ± 0.9 |
| Pioneer 3156 | 1.3 ± 0.4 | 2.1 ± 0.4 |
| Sc229-1 | 1.8 ± 0.6 | 3.1 ± 0.3 |
| Sc229-2 | 1.4 ± 0.4 | 3.1 ± 0.4 |
| Avg.[z] | 1.4 ± 0.2 | 3.0 ± 0.5 |
| Nodal sections (MS) | | |
| Dekalb 683 | 1.1 ± 0.3 | 3.3 ± 0.4 |
| Pioneer 3085 | 1.2 ± 0.4 | 3.2 ± 0.4 |
| Pioneer 3156 | 1.1 ± 0.3 | 3.6 ± 0.4 |
| Sc229-1 | 1.1 ± 0.3 | 3.1 ± 0.4 |
| Sc229-2 | 1.7 ± 0.4 | 2.9 ± 0.3 |
| Avg. | 1.2 ± 0.2 | 3.2 ± 0.2 |
| Immature zygotic embryos | | |
| Dekalb 683 | 1.8 ± 0.5 | 4.6 ± 0.5 |
| Pioneer 3085 | 1.4 ± 0.4 | 4.3 ± 0.4 |
| Pioneer 3156 | 1.5 ± 0.4 | 4.0 ± 0.4 |
| Sc229-1 | 2.4 ± 0.6 | 4.4 ± 0.5 |
| Sc229-2 | 2.6 ± 0.5 | 2.8 ± 0.8 |
| Avg. | 1.9 ± 0.5 | 4.0 ± 0.6 |
| Mature zygotic embryos | | |
| Dekalb 683 | 4.9 ± 0.5 | 11.9 ± 0.7 |
| Pioneer 3085 | 4.8 ± 0.7 | 10.2 ± 1.1 |
| Pioneer 3156 | 6.3 + 0.4 | 10.1 + 0.7 |
| Sc229-1 | 4.7 ± 0.4 | 10.3 ± 0.8 |
| Sc229-2 | 4.9 ± 0.5 | 9.8 ± 1.0 |
| Avg. | 5.1 ± 0.6 | 10.5 ± 0.7 |

Number represent mean number of GUS-positive sectors (blue spots) ± standard deviation of three random samples taken per plate bombarded with pAHC25, with 3 replicate plates sampled
[z]Average calculated value ± standard deviation among those numbers within fresh/frozen tungsten micro-projectiles Determination of Optimal DNA Concentration Three DNA concentrations, 1.0, 2.0 and 3.0 µg/µl (resulting in 1.0 µg, 2.0 µg and 3.0 µg per shot, respectively, using the standard DNA precipitation protocol) were compared in bombardments of the four explant sources from the four genotypes. Bombardments were conducted at 650 psi, with 720 µg 1.6 µm frozen tungsten per shot and 1.0 cm gap distance. Results determined that the lowest DNA concentration (1.0 µg/shot) yielded greater numbers of GUS-positive sectors within and among the genotypes for all four explant sources (Table 21). The numbers of GUS-positive sectors appeared to decrease with increasing DNA concentrations.

TABLE 21

Evaluation of optimal DNA concentration determined in transient GUS assays three days post-bombardment on nodal sections excised from germinated immature embryos (IS) and mature (MS) seedlings, and immature and mature zygotic embryos from four maize genotypes.

| | DNA Concentration (µg/shot) | | |
|---|---|---|---|
| | 1.0 | 2.0 | 3.0 |
| Genotype | No. GUS positive sectors/explant | | |
| Nodal sections (IS) | | | |
| Dekalb 683 | 3.2 ± 0.4 | 1.3 ± 0.4 | 0.6 ± 0.5 |
| Pioneer 3085 | 3.4 ± 0.5 | 2.1 ± 0.5 | 0.3 ± 0.5 |
| Pioneer 3156 | 3.6 ± 0.5 | 1.9 ± 0.6 | 0.3 ± 0.5 |
| Sc229-1 | 3.2 ± 0.4 | 1.2 ± 0.4 | 0.2 ± 0.4 |
| Sc229-2 | 3.0 ± 0.7 | 1.2 ± 0.4 | 1.1 ± 0.3 |
| Avg.[z] | 3.3 ± 0.2 | 1.5 ± 0.4 | 0.5 ± 0.3 |
| z,9/32 Nodal sections (MS) | | | |
| Dekalb 683 | 3.1 ± 0.3 | 1.1 ± 0.3 | 0.4 ± 0.4 |
| Pioneer 3085 | 3.3 ± 0.4 | 1.4 ± 0.4 | 0.9 ± 0.4 |
| Pioneer 3156 | 3.2 ± 0.4 | 1.7 ± 0.4 | 0.6 ± 0.4 |
| Sc229-1 | 3.4 ± 0.4 | 1.6 ± 0.4 | 1.3 ± 0.3 |
| Sc229-2 | 3.3 ± 0.4 | 1.9 ± 0.6 | 0.5 ± 0.4 |
| Avg. | 3.3 ± 0.1 | 1.5 ± 0.3 | 0.7 ± 0.3 |
| Immature zygotic embryos | | | |
| Dekalb 683 | 4.2 ± 0.6 | 1.2 ± 0.4 | 0.3 ± 0.5 |
| Pioneer 3085 | 3.3 ± 0.4 | 1.3 ± 0.4 | 1.2 ± 0.4 |
| Pioneer 3156 | 3.0 ± 0.7 | 1.3 ± 0.4 | 1.1 ± 0.3 |
| Sc229-1 | 4.1 ± 0.6 | 2.1 ± 0.5 | 0.9 ± 0.8 |
| Sc229-2 | 3.6 ± 0.5 | 1.3 ± 0.4 | 0.9 ± 0.8 |
| Avg. | 3.6 ± 0.5 | 1.4 ± 0.3 | 0.9 ± 0.3 |
| Mature zygotic embryos | | | |
| Dekalb 683 | 9.3 ± 0.7 | 3.3 ± 0.4 | 2.9 ± 0.4 |
| Pioneer 3085 | 9.6 ± 1.0 | 2.2 ± 0.4 | 2.1 ± 0.5 |
| Pioneer 3156 | 9.1 ± 1.2 | 3.6 ± 0.5 | 1.9 ± 0.6 |
| Sc229-1 | 8.1 ± 0.6 | 3.3 ± 0.4 | 2.7 ± 0.4 |
| Sc229-2 | 8.9 ± 0.9 | 2.2 ± 0.4 | 1.9 ± 0.6 |
| Avg. | 9.0 ± 0.5 | 2.9 ± 0.6 | 2.3 ± 0.4 |

Number represent mean number of GUS-positive sectors (blue spots) ± standard deviation of three random samples taken per plate bombarded with pAHC25, with 3 replicate plates sampled
[z]Average calculated value ± standard deviation among those numbers within each DNA concentration/per shot Evaluation of Optimal $CaCl_2$ Concentration for DNA Precipitation DNA (1.0 µg/µl) was precipitated in separate reactions onto 1.6 µm tungsten micro-projectiles utilizing four concentrations (0.5, 1.0, 1.5, 2.5 M) of $CaCl_2$. Bombardments were conducted on the target explant types from four genotypes at 650 psi using 1.0 µg DNA/shot, 720 µg 1.6 µm frozen tungsten/shot and a 1.0 cm gap distance. Although all initial precipitation protocols utilized 2.5 M $CaCl_2$ (Bio-Rad instruction manual), previously, it had not been determined optimal. However, results indicated that 2.5 M $CaCl_2$ in fact yielded greater numbers of GUS-positive sectors per explant within and among genotypes. At 2.5 M, some differences between genotypes within two of the explant sources were noted.

Optimization of $CaCl_2$ concentration was deemed important due to a conflicting report which determined that lower concentrations were better. Klein et al., 1988c, obtained greater numbers of GUS-positive sectors in transient assays post-bombardment in maize BMS cells after using 0.24 and 1.9 M $CaCl_2$ for DNA precipitation compared to 2.4 M. Our results indicated that lower concentrations, 0.5–2.0 M yielded lower numbers of GUS-positive sectors per explant, irrespective of genotype.

TABLE 22

Evaluation of optimal CaCl$_2$ concentration determined in transient GUS assays three days post-bombardment on nodal sections excised from germinated immature embryos (IS) and mature (MS) seedlings, and immature and mature zygotic embryos from four maize genotypes.

| Genotype | Ca$_2$Cl Concentration (M) | | | |
|---|---|---|---|---|
| | 0.5 | 1.0 | 1.5 | 2.5 |
| | No. GUS positive sectors/explant | | | |
| Nodal sections (IS) | | | | |
| Dekalb 683 | 1.2 ± 0.4 | 1.3 ± 0.4 | 1.5 ± 0.4 | 3.1 ± 0.3 |
| Pioneer 3085 | 1.4 ± 0.4 | 2.1 ± 0.5 | 1.3 ± 0.4 | 3.3 ± 0.4 |
| Pioneer 3156 | 1.6 ± 0.4 | 1.9 ± 0.6 | 1.3 ± 0.4 | 3.2 ± 0.4 |
| Sc229-1 | 1.2 ± 0.4 | 1.2 ± 0.4 | 1.2 ± 0.4 | 3.4 ± 0.5 |
| Sc229-2 | 2.0 ± 0.3 | 1.2 ± 0.4 | 1.1 ± 0.3 | 3.3 ± 0.4 |
| Avg.[z] | 1.5 ± 0.3 | 1.5 ± 0.3 | 1.3 ± 0.1 | 3.2 ± 0.1 |
| Nodal sections (MS) | | | | |
| Dekalb 683 | 1.1 ± 0.3 | 1.4 ± 0.4 | 1.2 ± 0.4 | 3.2 ± 0.4 |
| Pioneer 3085 | 1.2 ± 0.4 | 1.2 ± 0.4 | 2.1 ± 0.5 | 3.3 ± 0.4 |
| Pioneer 3156 | 1.6 ± 0.4 | 1.6 ± 0.4 | 1.9 ± 0.6 | 2.9 ± 0.3 |
| Sc229-1 | 1.7 ± 0.4 | 1.7 ± 0.4 | 1.6 ± 0.4 | 3.3 ± 0.4 |
| Sc229-2 | 1.9 ± 0.6 | 1.9 ± 0.6 | 1.5 ± 0.4 | 3.0 ± 0.5 |
| Avg. | 1.5 ± 0.3 | 1.4 ± 0.1 | 1.7 ± 0.3 | 3.1 ± 0.2 |
| Immature zygotic embryos | | | | |
| Dekalb 683 | 1.2 ± 0.5 | 2.3 ± 0.3 | 2.3 ± 0.4 | 4.3 ± 0.4 |
| Pioneer 3085 | 1.3 ± 0.5 | 1.9 ± 0.6 | 1.9 ± 0.4 | 3.6 ± 0.5 |
| Pioneer 3156 | 2.0 ± 0.4 | 1.7 ± 0.4 | 2.1 ± 0.6 | 3.4 ± 0.5 |
| Sc229-1 | 2.1 ± 0.4 | 2.1 ± 0.4 | 1.9 ± 0.4 | 4.1 ± 0.6 |
| Sc229-2 | 1.6 ± 0.6 | 2.3 ± 0.3 | 1.9 ± 0.4 | 3.0 ± 0.5 |
| Avg. | 1.6 ± 0.3 | 2.0 ± 0.1 | 2.0 ± 0.4 | 3.7 ± 0.4 |
| Mature zygotic embryos | | | | |
| Dekalb 683 | 4.3 ± 0.4 | 5.1 ± 0.7 | 6.2 ± 0.4 | 11.0 ± 0.7 |
| Pioneer 3085 | 5.6 ± 0.6 | 5.2 ± 0.7 | 5.9 ± 0.6 | 9.6 ± 1.0 |
| Pioneer 3156 | 6.1 ± 0.6 | 5.6 ± 1.1 | 6.1 ± 0.9 | 10.2 ± 1.1 |
| Sc229-1 | 8.1 ± 0.6 | 6.3 ± 1.0 | 5.9 ± 0.6 | 11.3 ± 0.7 |
| Sc229-2 | 8.2 ± 0.4 | 6.2 ± 1.0 | 6.2 ± 0.4 | 9.3 ± 0.7 |
| Avg. | 6.5 ± 1.4 | 5.8 ± 0.5 | 5.2 ± 0.1 | 10.3 ± 0.7 |

Number represent mean number of GUS-positive sectors (blue spots) ± standard deviation of three random samples taken per plate bombarded with pAHC25, with 3 replicate plates sampled
[z]Average calculated value ± standard deviation among those numbers within each CaCl$_2$ concentration

Evaluation of Tungsten Micro-Projectiles Delivered Per Shot

Three different concentration (per shot: 60, 300 and 720 μg) of 1.6 μm frozen tungten micro-projectiles were precipitated using the standard procedure (2.5 M CaCl$_2$) in separate reactions with pAHC25 DNA (1.0 μg/μl; 1.0 μg per shot). They were evaluated in bombardments at 650 psi with a 1.0 cm gap distance using the target tissue types and the four genotypes. As stated, all previous bombardments utilized 720 μg DNA-coated micro-projectiles per shot, but lower concentrations had not been evaluated. Results determined that delivery of 720 μg micro-projectiles per shot yielded greater numbers of GUS-positive sectors regardless of target tissue type within and among genotypes (Table 23). Exceptions were noted in MS, where Pioneer 3085, Sc229-1 and Sc220-2 (60 μg/shot) and Pioneer 3156 (300 μg) yielded comparable numbers. At 720 μg, some genotypic differences were noted within two explant sources. Within immature zygotic embryos, Dekalb 683 and Sc229-1 displayed greater numbers of GUS-positive sectors than Pioneer 3156 and Sc229-2. Similarly, Dekalb 683 and Pioneer 3082 mature zygotic embryos outperformed Pioneer 3156 (Table 23). However, all explant sources from all four genotypes were capable of DNA uptake. Since most of the protocol had been optimized utilizing 720 μg tungsten micro-projectiles, it was not surprising that it was confirmed to be the optimal quantity. This amount was higher compared to that reported by Klein et al., 1988c, who determined that bombardment of maize BMS suspension cells with tungsten at 150–200 μg per shot caused a zone of dead cells. However, those researchers utilized small cell clumps as targets which were determined to be more sensitive to the quantity of tungsten delivered.

TABLE 23

Evaluation of optimal tungsten micro-projectiles delivered per shot determined in transient GUS assays three days post-bombardment on nodal sections excised from germinated immature embryos (IS) and mature (MS) seedlings, and immature and mature zygotic embryos from four maize genotypes.

| Genotype | Tungsten Micro-Projectiles Delivered (μg/shot) | | |
|---|---|---|---|
| | 60 | 300 | 720 |
| | No. GUS positive sectors/explant | | |
| Nodal sections (IS) | | | |
| Dekalb 683 | 1.5 ± 0.4 | 2.3 ± 0.3 | 3.3 ± 0.4 |
| Pioneer 3085 | 1.7 ± 0.4 | 2.2 ± 0.4 | 3.7 ± 0.5 |
| Pioneer 3156 | 1.7 ± 0.4 | 1.9 ± 0.6 | 3.3 ± 0.4 |
| Sc229-1 | 1.3 ± 0.4 | 1.7 ± 0.4 | 3.1 ± 0.3 |
| Sc229-2 | 1.5 ± 0.6 | 1.5 ± 0.6 | 3.6 ± 0.5 |
| Avg.[z] | 1.5 ± 0.1 | 1.9 ± 0.3 | 3.4 ± 0.2 |
| Nodal sections (MS) | | | |
| Dekalb 683 | 1.1 ± 0.3 | 2.1 ± 0.5 | 3.3 ± 0.4 |
| Pioneer 3085 | 2.4 ± 0.6 | 1.9 ± 0.6 | 3.1 ± 0.3 |
| Pioneer 3156 | 1.4 ± 0.4 | 2.7 ± 0.4 | 3.6 ± 0.5 |
| Sc229-1 | 2.6 ± 0.7 | 2.3 ± 0.3 | 3.2 ± 0.4 |
| Sc229-2 | 1.8 ± 0.6 | 1.5 ± 0.6 | 2.7 ± 0.4 |
| Avg. | 1.9 ± 0.6 | 2.1 ± 0.4 | 3.2 ± 0.3 |
| Immature zygotic embryos | | | |
| Dekalb 683 | 1.1 ± 0.3 | 1.9 ± 0.6 | 4.4 ± 0.5 |
| Pioneer 3085 | 1.6 ± 0.4 | 2.2 ± 0.4 | 3.7 ± 0.5 |
| Pioneer 3156 | 1.3 ± 0.4 | 2.1 ± 0.5 | 3.1 ± 0.3 |
| Sc229-1 | 2.2 ± 0.4 | 2.9 ± 0.3 | 4.6 ± 0.5 |
| Sc229-2 | 2.3 ± 0.3 | 1.9 ± 0.6 | 3.2 ± 0.4 |
| Avg. | 1.7 ± 0.5 | 2.2 ± 0.4 | 3.8 ± 0.6 |
| Mature zygotic embryos | | | |
| Dekalb 683 | 4.3 ± 0.4 | 4.9 ± 0.5 | 10.3 ± 0.8 |
| Pioneer 3085 | 5.2 ± 0.6 | 4.3 ± 0.4 | 10.3 ± 0.8 |
| Pioneer 3156 | 4.6 ± 0.5 | 3.9 ± 0.5 | 8.6 ± 0.5 |
| Sc229-1 | 4.3 ± 0.4 | 3.7 ± 0.5 | 9.1 ± 1.2 |
| Sc229-2 | 2.7 ± 0.4 | 3.9 ± 0.7 | 9.9 ± 0.9 |
| Avg. | 4.2 ± 0.8 | 4.1 ± 0.4 | 9.7 ± 0.7 |

Number represent mean number of GUS-positive sectors (blue spots) ± standard deviation of three random samples taken per plate bombarded with pAHC25, with 3 replicate plates sampled
[z]Average calculated value ± standard deviation among those numbers within each concentration of tungsten delivered/shot

Determination of Optimal Gap Distance

Three different gap distances (0.32, 0.65 and 1.0 cm) were compared in bombardments conducted at 650 psi helium pressure using 1.0 μg DNA and 720 μg frozen 1.6 μm tungsten per shot using the standard precipitation protocol. As always, all target tissues from genotypes were compared for responses (Table 24). Results determined that bombardments with a gap distance of 1.0 cm yielded greater numbers of GUS-positive sectors per explant on three of the four target tissue types, while mature seedling nodal sections from all genotypes yielded greater numbers of GUS-positive sectors, within and among genotypes when a gap distance of 0.65 cm was used (Table 24). At that optimal gap distance, no genotypic differences were noted. This was the first difference noted between the four target explant types in regard to optimization of biolistic-associated variables. Mature nodal section explants may have had cell walls that were slightly harder to penetrate compared to other targets. The shorter distance between rupture disk and macro-projectile may have enhanced micro-projectile velocity which allowed for greater penetration of those explants. No quantitative or qualitative data were available in the literature regarding optimization of gap distances. With the results obtained, it was clear that gap distances were important and could vary depending on the target tissue explant utilized.

TABLE 24

Evaluation of optimal gap distance determined in transient GUS assays three days post-bombardment on nodal sections excised from germinated immature embryos (IS) and mature (MS) seedlings, and immature and mature zygotic embryos from four maize genotypes

| | Gap Distance (cm) | | |
|---|---|---|---|
| | 0.32 | 0.65 | 1.0 |
| Genotype | No. GUS positive sectors/explant | | |
| Nodal sections (IS) | | | |
| Dekalb 683 | 1.4 ± 0.4 | 2.1 ± 0.5 | 3.2 ± 0.4 |
| Pioneer 3085 | 1.7 ± 0.4 | 2.3 ± 0.5 | 3.6 ± 0.5 |
| Pioneer 3156 | 1.4 ± 0.4 | 1.6 ± 0.4 | 3.1 ± 0.3 |
| Sc229-1 | 1.2 ± 0.4 | 1.4 ± 0.4 | 2.9 ± 0.3 |
| Sc229-2 | 1.6 ± 0.4 | 1.1 ± 0.3 | 3.3 ± 0.4 |
| Avg.[z] | 1.5 ± 0.2 | 1.7 ± 0.4 | 3.2 ± 0.2 |
| Nodal sections (MS) | | | |
| Dekalb 683 | 1.3 ± 0.3 | 3.2 ± 0.4 | 1.7 ± 0.4 |
| Pioneer 3085 | 1.6 ± 0.4 | 2.9 ± 0.3 | 1.5 ± 0.3 |
| Pioneer 3156 | 1.2 ± 0.4 | 3.3 ± 0.4 | 1.7 ± 0.4 |
| Sc229-1 | 1.7 ± 0.4 | 3.1 ± 0.3 | 1.3 ± 0.4 |
| Sc229-2 | 1.9 ± 0.6 | 2.9 ± 0.3 | 1.2 ± 0.4 |
| Avg. | 1.5 ± 0.2 | 3.0 ± 0.2 | 1.5 ± 0.2 |
| Immature zygotic embryos | | | |
| Dekalb 683 | 1.1 ± 0.3 | 1.3 ± 0.4 | 4.2 ± 0.4 |
| Pioneer 3085 | 1.9 ± 0.6 | 2.0 ± 0.7 | 3.9 ± 0.5 |
| Pioneer 3156 | 2.3 ± 0.3 | 2.3 ± 0.3 | 3.7 ± 0.7 |
| Sc229-1 | 2.6 ± 0.5 | 1.9 ± 0.6 | 4.2 ± 0.4 |
| Sc229-2 | 2.7 ± 0.4 | 1.8 ± 0.6 | 3.3 ± 0.4 |
| Avg. | 2.1 ± 0.6 | 1.9 ± 0.3 | 3.9 ± 0.3 |
| Mature zygotic embryos | | | |
| Dekalb 683 | 4.7 ± 0.4 | 5.1 ± 0.7 | 10.7 ± 0.8 |
| Pioneer 3085 | 5.1 ± 0.7 | 4.2 ± 0.4 | 11.6 ± 0.8 |
| Pioneer 3156 | 5.6 ± 0.6 | 4.3 ± 0.4 | 9.7 ± 0.5 |
| Sc227 | 4.9 ± 0.5 | 3.8 ± 0.6 | 10.1 ± 0.7 |
| S1229 | 3.9 ± 0.7 | 2.6 ± 0.7 | 9.8 ± 1.0 |
| Avg. | 4.8 + 0.6 | 4.0 ± 0.8 | 10.4 ± 0.7 |

Number represent mean number of GUS-positive sectors (blue spots) ± standard deviation of three random samples taken per plate bombarded with pAHC25, with 3 replicate plates sampled
[z]Average calculated value ± standard deviation among those numbers within each gap distance Determination of Optimal Plating Density of Target Tissues Two different plating densities for each target tissue type from the four genotypes were compared. Nodal sections from germinated immature embryos and mature seedlings (40 versus 50 sections per plate), immature zygotic embryos (30 versus 35 embryos per plate) and mature zygotic embryos (24 versus 30 embryos per plate) were closely compacted in a circle (completely filled) in the central 2.5 cm diameter area of the petri plate. All bombardments utilized helium at 650 psi with 1.0 µg DNA and 720 µg frozen 1.6 µm tungsten micro-projectiles per shot (standard precipitation), and optimal gap distance per target tissue (1.0 or 0.65 cm). As stated earlier, in previous experiments, standard numbers of explants per plate (per shot) were the lower values listed in each comparison. Results determined that the lower numbers of explants (40 immature and mature nodal sections, 30 immature zygotic embryos and 24 mature zygotic embryos) targeted per bombardment yielded greater numbers of GUS-positive sectors per explant within and among genotypes (exceptions: Pioneer 3085 MS, Sc-229-2 immature zygotic embryos; Table 25). Within optimal numbers of explants per plate, one difference between genotypes was noted. In immature zygotic embryos, Dekalb 683 displayed greater numbers of GUS-positive sectors than Pioneer 3085 and Sc229-2 (Table 25).

TABLE 25

Evaluation of optimal explant plating densities determined in transient GUS assays three days post-bombardment on nodal sections excised from germinated immature embryos (IS) and mature (MS) seedlings, and immature and mature zygotic embryos from four maize genotypes

| Genotype | No. GUS Positive Sectors/Explant | |
|---|---|---|
| Nodal sections (IS) | | |
| | 40 per plate[2] | 50 per plate |
| Dekalb 683 | 3.6 ± 0.5 | 2.1 ± 0.4 |
| Pioneer 3085 | 3.9 ± 0.5 | 2.2 ± 0.4 |
| Pioneer 3156 | 3.3 ± 0.4 | 1.3 ± 0.4 |
| Sc229-1 | 3.3 + 0.4 | 1.9 ± 0.6 |
| Sc229-2 | 3.2 ± 0.4 | 1.6 ± 0.4 |
| Avg.[y] | 3.5 ± 0.3 | 1.8 ± 0.3 |
| Nodal sections (MS) | | |
| | 40 per plate | 50 per plate |
| Dekalb 683 | 3.1 ± 0.3 | 2.2 ± 0.4 |
| Pioneer 3085 | 3.0 ± 0.5 | 2.3 ± 0.3 |
| Pioneer 3156 | 3.2 ± 0.4 | 1.3 ± 0.4 |
| Sc229-1 | 3.3 ± 0.4 | 1.9 ± 0.6 |
| Sc229-2 | 3.6 ± 0.5 | 2.3 ± 0.3 |
| Avg. | 3.2 ± 0.2 | 2.1 ± 0.2 |
| Immature zygotic embryos | | |
| | 30 per plate | 35 per ptate |
| Dekalb 683 | 4.6 ± 0.5 | 1.3 ± 0.4 |
| Pioneer 3085 | 3.3 ± 0.4 | 1.2 ± 0.4 |
| Pioneer 3156 | 3.6 ± 0.5 | 1.9 ± 0.6 |
| Sc229-1 | 4.2 ± 0.4 | 2.2 ± 0.4 |
| Sc229-2 | 3.1 ± 0.3 | 2.4 ± 0.6 |
| Avg. | 3.7 ± 0.5 | 1.8 ± 0.5 |
| Mature zygotic embryos | | |
| | 24 per plate | 30 per plate |
| Dekalb 683 | 9.1 ± 1.2 | 4.1 ± 0.6 |
| Pioneer 3085 | 10.2 ± 1.1 | 5.9 ± 0.6 |
| Pioneer 3156 | 10.1 ± 0.7 | 6.3 ± 0.4 |
| Sc229-1 | 9.8 ± 1.0 | 5.7 ± 0.5 |
| Sc229-2 | 9.3 ± 0.7 | 5.8 ± 0.4 |
| Avg. | 9.7 ± 0.4 | 5.7 ± 0.8 |

Number represent mean number of GUS-positive sectors (blue spots) ± standard deviation of three random samples taken per plate bombarded with pAHC25, with 3 replicate plates sampled
[z]No. of explants arranged compactly inside a 2.5 cm diameter circle per plate (replicate)
[y]Average calculated value ± standard deviation among those numbers within each plating density
No quantitative data comparing plating densities for target tissues could be identified in the literature.

in the literature. Routine maize transformation protocols frequently utilized suspension cells as targets, Gordon-Kamm et al., 1990, Fromm et al., 1990, in which densities could not be used for comparisons to explant numbers in this research. Hill et al., 1995, targeted 36 immature embryos (14–15 dpp) per bombardment utilizing a helium pressure of 1550 psi, 1.0 µm gold particles and a target distance of 8.0 cm. Our results determined that plating densities of target explants may be an important factor for efficient gene delivery.

Genotype-Independence of the Bombardment Protocols

Different target tissues excised from 21 maize genotypes were compared for numbers of GUS-positive sectors determined per explant after bombardments. These bombardments were performed utilizing optimized parameters obtained in pre-screening of the four genotypes (commercial hybrids: Dekalb 683, Pioneer 3085, Pioneer 3156; inbreds: Sc229-1 and Sc229-2). mature seedling nodal sections were identified as unique targets, the first such report for maize biolistic transformation-optimization protocols.

TABLE 26

Results of the transient GUS assays conducted three days post-bombardment utilizing optimal biolistic parameters on nodal sections excised from germinated immature embryos (IS) and mature (MS) seedlings, and immature and mature zygotic embryos from 21 genotypes.

Mean Number GUS-Positive (Blue) Sectors Per Explant

| | | Nodal sections (dia: 1.2–1.5 mm) | | Zygotic embryos | |
|---|---|---|---|---|---|
| | | | | Immature | Mature |
| | Genotype | IS | MS | (length: 1.5 mm) | (length: 3.0–5.0 mm) |
| Grain hybrids | Agratech 810 | 2.1 ± 0.5 | 2.1 ± 0.5 | 2.0 ± 0.5 | 9.3 ± 0.7 |
| | Agratech 888F4 | 3.0 ± 0.7 | 2.7 ± 0.7 | 3.0 ± 0.7 | 10.1 ± 0.7 |
| | Asgrow Rx897 | 3.3 ± 0.2 | 3.3 ± 0.2 | 3.3 ± 0.4 | 9.8 ± 1.0 |
| | Asgrow Rx899 | 3.3 ± 0.2 | 3.1 ± 0.4 | 4.2 ± 0.6 | 9.7 ± 0.5 |
| | Cargill X9255 | 1.6 ± 0.4 | 2.6 ± 0.4 | 3.6 ± 0.5 | 10.2 ± 0.3 |
| | Cargill 8327 | 2.6 ± 0.5 | 3.2 ± 0.4 | 4.2 ± 0.6 | 10.4 ± 0.7 |
| | Dekalb 649 | 3.3 ± 0.2 | 2.1 ± 0.5 | 4.1 ± 0.6 | 10.2 ± 0.3 |
| | Dekalb 683 | 3.0 ± 0.7 | 3.3 ± 0.2 | 4.1 ± 0.6 | 10.6 ± 0.7 |
| | ICI 8281 | 2.1 ± 0.5 | 1.1 ± 0.3 | 2.6 ± 0.5 | 10.2 ± 0.3 |
| | Northrup King n7787 | 2.6 ± 0.5 | 3.3 ± 0.2 | 4.2 ± 0.6 | 11.9 ± 0.7 |
| | Northrup King n8811 | 2.4 ± 0.6 | 3.1 ± 0.4 | 3.0 ± 0.7 | 9.8 ± 1.0 |
| | Pioneer 3085 | 2.6 ± 0.5 | 3.3 ± 0.2 | 4.2 ± 0.6 | 11.9 ± 0.7 |
| | Pioneer 3145 | 2.6 ± 0.5 | 1.6 ± 0.4 | 3.0 ± 0.7 | 10.3 ± 0.8 |
| | Pioneer 3156 | 1.3 ± 0.4 | 2.4 ± 0.6 | 4.2 ± 0.6 | 9.6 ± 1.0 |
| | Pioneer 3167 | 2.6 ± 0.6 | 2.1 ± 0.5 | 3.0 ± 0.7 | 10.6 ± 0.7 |
| | TR 1185 | 1.6 ± 0.4 | 2.6 ± 0.5 | 2.6 ± 0.6 | 10.6 ± 0.7 |
| Sweet corn hybrid | Funks G90 | 1.8 ± 0.5 | 2.0 ± 0.5 | 2.6 ± 0.6 | 10.6 ± 0.7 |
| Inbreds | Mp708 | 2.4 ± 0.6 | 3.0 ± 0.7 | 4.1 ± 0.6 | 9.6 ± 1.0 |
| | Sc229-1 | 1.6 ± 0.4 | 2.1 ± 0.5 | 4.2 ± 0.6 | 10.3 ± 0.7 |
| | Sc229-2 | 3.3 ± 0.2 | 2.6 ± 0.5 | 2.4 ± 9.6 | 9.6 ± 1.0 |
| | Tx601 | 1.4 ± 0.4 | 2.1 ± 0.5 | 4.1 ± 0.6 | 10.3 ± 0.8 |
| | Va35 | 2.1 ± 0.5 | 1.3 ± 0.4 | 4.2 ± 0.6 | 9.6 ± 1.0 |
| Avg.[z] | | 2.2 ± 0.7 | 2.2 ± 0.7 | 3.3 ± 0.7 | 9.9 ± 1.1 |

Number represent mean number of GUS-positive sectors (blue spots) ± standard deviation of three random samples taken per plate bombarded with pAHC25, with 3 replicate plates sampled
[z]Averaged calculated value ± standard deviation among those numbers within each explant source Results indicated that the protocol for each explant source was genotype-independent in regard to successful delivery of DNA. In each target tissue, all 21 genotypes displayed at least one GUS-positive sector per explant (Table 26). As in all previous experiments, bombardments with pBI101.2 yielded zero blue spots. Numbers of GUS-positive sectors ranged from 1.1–3.3 for immature and mature nodal sections, 2.0–4.2 and 9.3–11.9 per immature and mature zygotic embryo respectively (Table 26).

Within each explant type, some genotypes displayed greater numbers of GUS-positive sectors. In IS, Asgrow hybrids and Dekalb 649 outperformed 11 genotypes, but performed similar to eight others (Table 26).

Biolistic protocols for maize, thus far, have been optimized for specific targets such as suspension cultures from a few maize genotypes that include BMS, and A188 and B73 crosses, Klein et al., 1988; Gordon-Kamm et al., 1990; Walters et al., 1992. Our optimized protocols for the four target tissue types were proven genotype-independent in transient GUS assays with respect to ability to efficiently introduce DNA into al 21 genotypes tested. Interestingly, the developed protocols did not differ with respect to the biolistic parameters for all target tissues (except the gap distance: 0.65 cm for nodal sections from mature seedlings). Similarities and genotype-independence of the protocols for all target tissues are advantageous in that the user need not change the biolistic parameters and could use the PDS-1000/He® with ease for foreign DNA delivery into all target tissues from different maize genotypes. Immature and Screening In vitro regeneration and biolistic DNA delivery protocols were developed for maize utilizing juvenile explant sources: nodal sections excised from germinated embryos (immature) and seedlings (from mature seeds). Organogenic regeneration protocols were initially developed for four hybrid and inbred maize genotypes. The genotype-independence of each protocol was confirmed by successful regeneration of 21 maize genotypes which included 16 commercial grain hybrids, one sweet corn hybrid and four inbred lines.

An adventitious shoot regeneration protocol was developed utilizing nodal sections excised from germinated immature embryos (matured in vitro) and mature seedlings. Optimal numbers of shoots were obtained on a MS-based medium (A) containing 3% sucrose (w/v), 0.25 mg/l CPA plus 2.0 mg/l BAP. Excised shoots elongated and rooted on a MS-based medium containing 0.5 mg/l IBA. Explants were harvested from germinated embryos (immature) or seedlings (mature). Use of mature seeds would ease the season- and time-dependence of immature explant availability/receptivity. This would also aid transformation efforts due to the abundance of mature seeds year-round and the ability to store them until needed.

Biolistic protocols using the PDS-1000He® apparatus were optimized via transient GUS histochemical assays following bombardment with GUS-encoded pAHC25 DNA coated onto tungsten micro-projectiles. Optimizations were conducted on each of the target tissues from the four (hybrid and inbred) genotypes. The developed biolistic protocols were each confirmed to be genotype-independent after successful introduction of pAHC25 DNA into cells of all four target tissues harvested from 21 maize genotypes. Optimal bombardment protocols utilized 40 nodal sections, 30 immature or 24 mature zygotic embryos per petri plate, each organized in a 2.5 cm diameter circle. Plasmid pAHC25 DNA-coated 1.6 μm (M-25) tungsten micro-projectiles (frozen) were delivered at a velocity of 650 psi helium pressure with set gap (0.65 cm or 1.0 cm) and target (7.5 cm) distances. Approximately 1.0 μg pAHC25 DNA and 720 μg tungsten micro-projectiles delivered per shot were optimal. The developed protocols were determined genotype-independent after successful delivery of foreign DNA into all 21 genotypes for each target explant.

Currently, routine maize transformation protocols are restricted to a few target explants and agronomically important genotypes. With these inventive protocols, numerous agronomically important genotypes could be regenerated from explants which were also successfully used as targets in biolistics-based transformation protocols.

REFERENCES

1. Armstrong, C. L., and Green, C. E. 1985. Establishment and maintenance of friable embryogenic maize callus and involvement of L-proline. Planta 164:207–214.
2. Barton, K. A., and Brill, W. J. 1983. Prospects in plant genetic engineering. Science 219:671–675.
3. Batty, N. P., and Evans, J. M. 1992. Biological ballistics no longer a shot in the dark. Transgenic Res. 1:107–113.
4. Bio-Rad (Biolistic PDS-1000/He®) instruction manual. Bio-Rad laboratories, Hercules, Calif.
5. Brown, D. C. W., Tian, L., Buckley, D. J., Lefebvre, M., McGrath, A., and Webb, J. 1994. Development of a simple particle bombardment device for gene transfer into plant cells. Plant Cell. Tiss. Org. Cult. 37:47–53.
6. Callis, J., Fromm, M., and Walbot, V. 1987., Introns increase expression in cultured maize cells. Genes Dev. 1:1183–1200.
7. Cao, J., Wang, Y. C., Klein, T. M., Sanford, J. C., and Wu, R. 1990. Transformation of rice and maize using the biolistic process, p. 21–33. In: Lamb, C. J., and Beachy, R. N. (eds.), Plant gene transfer. Alan R. Liss, Inc., New York, N.Y.
8. Chassan, R. 1992. Transforming maize transformation. Plant Cell 4:1463–1464.
9. Cheng, T.-Y., and smith, H. H. 1975. Organogenesis from callus culture of Hordeum vulgare. Planta 123:307–310.
10. Chibbar, R. N., and Kartha, K. K. 1994. Transformation of plant cells by bombardment with micro-projectiles, p. 37–60. In: Shargool, P. D., and Ngo, T. T. (Eds.), Biotechnological applications of plant cultures. CRC Press, Ann Arbor, Mich.
11. Christensen, A. H., and Quail, P. H. 1996. Ubiquitin promoter-based vectors for high-level expression of selectable and/or screenable marker genes in monocotyledonous plants. Transgenic Res. 5:213–218.
12. Christou, P., Ford, T. L., and Kofron, M. 1991. Production of transgenic rice (Oryza sativa L.) plants from agronomically important indica and japonica varieties via electric discharge particle acceleration of exogenous DNA into immature zygotic embryos. Bio/Technol. 9:957–962.
13. Christou, P. 1993. Philosophy and practice of variety independent gene transfer into recalcitrant crops. In Vitro Cell. Dev. Biol. 29P: 119–124.
14. Chu, C. C., Wang, C. C., Sun, C. S., Hus, C., Yin, K. C., and Chu, C. Y. 1975. Establishment of an efficient medium for anther culture of rice through comparative experiments on the nitrogen sources. Scientia Sin. 18:659–668.
15. Cocking, E. C., and Davey, M. R. 1987. Gene transfer into cereals. Science 236:1259–1262.
16. Crossway, A., Oake, J. V., Irvine, J. M., Ward, B., Knauf, V. C., and Shewmaker, C. K. 1986. Integration of foreign DNA following micro-injection of tobacco mesophyll protoplasts. Mol. Gen. Genet. 202:179–185.
17. Dalton, S. J., and Dale, P. J. 1985. The application of in vitro tiller induction in Lolium multiflorum. Euphytica 34:897–904.
18. Dekeyser, R., Inze, D., and Van Montagu, M. 1990. Transgenic plants, p. 237–250. In: Gustafson, J. P. (Ed.), Gene manipulation in plant improvement II. Plenum Press, New York, N.Y.
19. Donath, M., Mendel, R., Cerff, R., and Martin, W. 1995. Intron-dependent transient expression of the maize GapAl gene. Plant Mol. Biol. 28:667–676.
20. Duncan, D. R., and Widholm, J. M. 1988. Improved plant regeneration from maize callus cultures using 6-benzylaminopurine. Plant Cell Rpt. 7:452–455.
21. Duncan, D. R., Williams, M. E., Zehr, B. E., and Widholm, J. M. 1985. The production of callus capable of regeneration from immature embryos of numerous Zea mays genotypes. Planta 165:322–332.
22. Finer, J. J., and McMullen, M. D. 1990. Transformation of cotton (Gossypium hirsutum L.) Via particle bombardment. Plant Cell Rpt. 8:586–589.
23. Fraley, R. T., Rogers, S. G., and Horsch, R. B. 1986. Genetic transformation of higher plants. CRC Crit. Rev. Plant Sci. 4:1–46.
24. Fromm, M. E., Morrish, F., Armstrong, C., Williams, R., Thomas, J. A., and Klein, T. M. 1990. Expression of chimeric genes in the progeny of transgenic maize plants. Bio/technol. 8:833–838.
25. Fromm, M. E., Taylor, L. P., and Walbot, V. 1985. Expression of genes transferred into monocot and dicot plant cells by electroporation. Proc. Natl. Acad. Sci. USA 82:5824–5828.
26. Fromm, M. E., Taylor, L. P., and Walbot, V. 1986. Stable transformation of maize after gene transfer by electroporation. Nature 319:791–793.
27. Gallagher, S. R. (Ed.). 1992. GUS protocols: using the GUS gene as a reporter of gene expression. Academic Press, San Diego, Calif.
28. Gamborg, O. L., Miller, R. A., and Ojiima, K. 1968. Nutrient requirement of suspension cultures of soybean root cells. Exp. Cell Res. 50:151–158.
29. Gamborg, O. L., Shyluk, J. P., Brar, D. S., and Constabel, F. 1977. Morphogenesis and plant regeneration from callus of immature embryos of sorghum. Plant Sci. Lett. 10:67–74.
30. Gasser, C. S., and Fraley, R. T. 1989. Genetically engineering plants for crop improvement. Science 244:1293–1299.
31. Goff, S. A., Klein, T. M., Roth, B. A., Fromm, M. E., Cone, K. C., Radicella, J. P., and Chandler, V. L. 1990. Transactivation of anthocyanin biosynthetic genes following transfer of B regulatory genes into maize tissues. EMBO J. 9:2517–2522.
32. Goldstein, C. S., and Kronstad, W. E. 1986. Tissue culture and plant regeneration from immature embryo explants of barley, Hordeum vulgare. Theor. Appl. Genet. 71:631–636.
33. Gordon-Kamm, W. J., Spencer, T. M., Mangano, M. L., Adams, T. R., Daines, R. J., Start, W. G., O'Brien, J. V., Chambers, S. A., Adams, W. R., Jr., Willetts, N. G., Rice, T. G., Mackey, C. J., Krueger, R. W., Kausch, A. P., and Lemaux, P. G. 1990. Transformation of maize cells and regeneration of fertile transgenic plants. Plant Cell 2:603–618.

34. Gould, J., Devey, M., Hasegawa, O., Ulian, E. C., Peterson, G., and Smith, R. H. 1991. Transformation of *Zea mays* L. using *Agrobacterium tumefaciens* and the shoot apex. Plant Physiol. 95:426–434.
35. Gray, D. J., Hebert, E., Lin, C. M., Compton, M. E., McCall, D. W., Harrison R. J., and Gaba, V. P. 1994. Simplified construction and performance of a device for particle bombardment. Plant Cell Tiss. Org. Cult. 37:179–184.
36. Green, C. E., and Phillips, R. L. 1975. Plant regeneration from tissue cultures of maize. Crop Sci. 15:417–421.
37. Grimsley, N. H., Ramos, C., Heine, T., and John, B. 1988. Meristematic tissues of maize plants are most susceptible to agro-infection with maize streak virus. Bio/Technol. 6:185–189.
38. Hagio, T., Blowers, A. D., and Earle, E. D. 1991. Stable transformation of sorghum cell culture after bombardment with DNA coated micro-projectiles. Plant Cell Rpt. 10:260–264.
39. He, M., A. Wilde, Kaderbhai, M. A. 1990. A simple single-step procedure for small-scale preparation of *Escherichia coli* plasmids. Nucleic Acids Res. 18:1660.
40. Hill, M., Launis, K., Bowman, C., McPherson, K., Dawson, J., Watkins, J., Koziel, M., and Wright, M. S. 1995. Biolistic introduction of a synthetic Bt gene into elite maize. Euphytica 85:119–123.
41. Hodges, T. K., Kamo, K. K., Imbrie, C. W., and Becwar, M. R. 1986. Genotype specificity of somatic embryogenesis and regeneration in maize. Bio/Technol. 4:219–223.
42. Irish, E. E., and Nelson, T. M. 1988. Development of maize plants from cultured shoot apices. Planta 175:9–12.
43. Ishida, Y., Saito, H., Ohta, S., Hiei, Y., Komari, T., and Kumashiro, T. 1996. High efficiency transformation of maize (*Zea mays* L.) Mediated by *Agrobacterium tumefaciens*. Bio/Technol. 14:745–750.
44. Jefferson, R. A. 1987. Assaying chimeric genes in plants: the GUS gene fusion system. Plant Mol. Biol. Rpt. 5:387–405.
45. Jeon, J.-S., Jung, H.-S., Sung, S.-K., Lee, J. S., Choi, Y. D., Kim, H.-J., and Lee, K.-W. 1994. Introduction and expression of foreign genes in rice cells by particle bombardment. J. Plant Biol. 37:27–36.
46. Kartha, K. K., Chibbar, R. N., Georges, F., Leung, N., Caswell, K., Kendall, E., and Qureshi, J. 1989. Transient expression of chloramphenicol acetyltransferase (CAT) gene in barley cell cultures and immature embryos through micro-projectile bombardment. Plant Cell Rpt. 8:429–432.
47. Kausch, A. P., Adams, T. R., Mangano, M., Zachwieja, S. J., Gordon-Kamm, W., Daines, R., Willetts, N. G., chambers, S. A., Adams, A., Jr., Anderson, A., Williams, G., Haines, G. 1995. Effects of micro-projectile bombardment on embryogenic suspension cell cultures of maize (*Zea mays* L.) Used for genetic transformation. Planta 196:501–509.
48. Kikkert, J. R. 1993. The biolistic PDS-1000/He® device. Plant Cell. Tiss. Org. Cult. 33:251–257.
49. King, P. K., and Kasha, K. J. 1994. Optimizing somatic embryogenesis and particle bombardment of barley (*Hordeum vulgare* L.) Immature embryos. In Vitro Cell. Dev. Biol. 30P:117–123.
50. Klein, T. M. 1990. Inheritance of chimeric genes in the progeny of transgenic maize plants. Bio/Technol. 9:833–838.
51. Klein, T. M., Arentzen, R., Lewis, P. A., and McEligott, S. F. 1992. Transformation of microbes, plants and animals by particle bombardment. Bio/Technol. 10:286–291.
52. Klein, T. M., Fromm, M. E., Weissenger, A., Tomes, D., Schaaf, S., Sletten, M., and Sanford, J. C. 1988a. Transfer of foreign genes into intact maize cells using high velocity micro-projectiles. Proc. Natl. Acad. Sci. USA 85:4305–4309.
53. Klein, T. M., Harper, E. C., Svab, Z., Sanford, J. C., Fromm, M. E., and Maliga, P. 1988b. Stable genetic transformation of intact Nicotiana cells by the particle bombardment process. Proc. Natl. Acad. Sci. USA 85:8502–8505.
54. Klein, T. M., Kornstein, K., Fromm, M. E., and Sanford, J. C. 1988c. Factors influencing gene delivery into *Zea mays* cells by high velocity micro-projectiles. Bio/Technol. 6:559–563.
55. Klein, T. M., Komstein, L., Sanford, J. C., and Fromm, M. E. 1989. Genetic transformation of maize cells by particle bombardment. Plant Physiol. 91:440–444.
56. Klein, T. M., Wolf, E. D., Wu, R., and Sanford, J. C. 1987. High velocity micro-projectiles for delivering nucleic acids into living cells. Nature 327:70–73.
57. Krens, F. H., Molendijk, L., Wullems, G. J., and Schilperoort, R. A. 1982. In vitro transformation of plant protoplasts with Ti-plasmid DNA. Nature 296:72–74.
58. Langer, R. H. M., and Hill, g. D. 1991. Agricultural plants. Cambridge Univ. Press, Cambridge, UK.
59. Last, D. I., Brettel, R. I. S., chamberlain, D. A., Chaudhury, A. M., Larkin, P. J., Marsh, E. L., Peacock, W. J., and Dennis, E. S. 1991. Pemu: an improved promoter for gene expression in cereal cells. Theor. Appl. Genet. 81:581–588.
60. Lin, M. S., Comings, D. E., and Alfi, O. S. 1977. Optical studies of the interaction of 4'-6-diamidino-2-phenylindole with DNA and metaphase chromosomes. Chromosoma 60:15–25.
61. Linsmaier, E., and Skoog, F. 1965. Organic growth factor requirements of tobacco tissue culture. Physiol. Plant. 18:100–127.
62. Lowe, K., Bowen, B., Hoerster, G., Ross, M., Bond, D., Pierce, D., and Gordan-Kamm, B. 1995. Germline transformation of maize following manipulation of chimeric shoot meristems. Bio/Technol. 13:667–681.
63. Lowe, K., Taylor, D. B., Ryan, P., and Paterson, K. E. 1985. Plant regeneration via organogenesis and embryogenesis in the maize inbred line B73. Plant Sci. 41:1125–132.
64. Lu, C., and Vasil, I. K. 1982. Somatic embryogenesis and plant regeneration in tissue cultures of *Panicum maximum* Jacq. Amer. J. Bot. 69:77–81.
65. Lu, C., Vasil, I. K., and Akins, O. P. 1982. Somatic embryogenesis in *Zea mays* L. Theor. Appl. Genet. 62:109–112.
66. Lu, C., Vasil, V., and Vasil, I. K. 1983. Improved efficiency of somatic embryogenesis and plant regeneration in tissue culture of maize (*Zea mays* L.). Theor. Appl. Genet. 66:285–289.
67. Ma, H., Gu, M., and Liang, G. H. 1987. Plant regeneration from cultured immature embryos of *Sorghum bicolor* (L.) Moench. Theor. Appl. Genet. 73:389–394.
68. Mackenzie, D. R., Anderson, P. M., and Wernham, C. C. 1966. A mobile air blast inoculator for plot experiments with maize dwarf mosaic virus. Plant Dis. Rpt. 50:363–367.
69. Maddock, S. E., Lancaster, V. A., Risiott, R., and Franklin, J. 1983. Plant regeneration from cultured immature embryos and inflorescences of 25 cultivars of wheat (*Triticum aestivum*). J. Exp. Bot. 34:915–926.
70. Mass, C., Lauffs, J., Grant, S., Korfhage, C., and Werr, W. 1991. The combination of a novel stimulatory element 70. (cont.) in the first exon of the maize Shrunken1 gene with the following intron 1 enhances reporter gene expression up to a 1000 fold. Plant Mol. Biol. 16:199–207.
71. McCabe, D., and Christou, P. 1993. Direct DNA transfer using electric discharge particle acceleration (ACCELL™ technology). Plant Cell. Tiss. Org. Cult. 33:227–236.
72. McElroy, D., Zhange, W., and Wu, R. 1990. Isolation of an efficient actin promoter for use in rice transformation. Plant Cell 2:163–171.
73. Mendel, R. R., Muller, B., Schultz, J., Kolesnikov, V., and Zelanin, A. 1989. Delivery of foreign genes to intact barley cells by high velocity micro-projectiles. Theor. Appl. Genet. 78:31–34.
74. Murashige, T., and Skoog, F. 1962. A revised medium for rapid growth and bioassays with tobacco tissue cultures. Physiol. Plant. 15:473–497.
75. Oard, J. H., Paige, D. F., Simmonds, J. A., and Gradziel, T. M. 1990. Transient gene expression in maize, rice and wheat cells using an airgun apparatus. Plant Physiol. 92:334–339.
76. Perl, A., Kless, H., Blumenthal, A., Galili, G., and Galun, E. 1992. Improvement of plant regeneration and GUS expression in scutellar wheat calli by optimization of culture conditions and DNA micro-projectiles delivery procedures. Mol. Gen. Genet. 235:279–284.
77. Perlak, F. J., Deaton, R. W., Armstrong, T. A., Fuchs, R. L., Sims, S. R., Greenplate, J. Y., and Fischoff, D. A. 1990. Insect resistant cotton plants. Bio/Technol. 8:939–943.
78. Potrykus, I. 1990. Gene transfer into cereals: an assessment. Trends Biotechnol. 7:269–273.
79. Power, J. B., and Cocking, E. C. 1977. Selection systems for somatic hybrids, p. 497–505. In: Reinhert, J., and Bajaj, Y. P. S. (eds.), Plant cell, tissue and organ culture. Springer-Verlag, New York, N.Y.
80. Raman, K., Walden, D. B., and Greyson, R. I. 1980. Propagation of *Zea mays* L. by shoot tip culture: a feasibility study. Ann. Bot. 45:183–189.
81. Ratnayaka, I. J. S., and Oard, J. H. 1995. A rapid method to monitor DNA precipitation onto micro-carriers before particle bombardment. Plant Cell Rpt. 14:794–798.
82. Redenbaugh, K., Hiatt, W., Martineau, B., Kramer, M., Sheehy, R., Sanders, R., Houck, C., and Emlay, D. 1992. Safety assessment of genetically engineered fruits and vegetables: a case study of the Flavr Savr tomato. CRC Press, Ann Arbor, Mich.
83. Rhodes, C. A., Lowe, K. S., and Ruby, K. L. 1988. Plant regeneration from protoplasts isolated from embryogenic maize cell cultures. Bio/Technol. 6:56–60.
84. Rhodes, C. A., Pierce, D. A., Mettler, I. J., Mascarenhas, D., and Detmer, J. J. 1988. Genetically transformed maize plants from protoplasts. Science 240:204–207.
85. Ritala, A., Aspergen, K., Kurten U., Martilla, M. S., Mannonen, L., Kauppinen, V., Teeri, T. H., and Enari, T. M. 1994. Fertile transgenic barley by particle bombardment of immature embryos. Plant Mol. Biol. 24:317–325.
86. Russell, J. A., Roy, M. K., and Sanford, J. C. 1992. Major improvements in biolistic transformation of suspension-cultured tobacco cells. In Vitro Cell Dev. Biol. 28P:97–105.
87. Sambrook, J., Fritsch, E. F., and Maniatis, J. 1989. Molecular cloning: a laboratory manual. Cold Spring Harbor Laboratory Press, Cold Spring Harbor, N.Y.
88. Sanford, J. C. 1988. The biolistic process. Trends Biotechnol. 6:299–302.
89. Sanford, J. C., Klein, T. M., Wolf, E. D., and Allen, N. K. 1987. Delivery of substances into cells and tissues using a particle bombardment process. Particulate Sci. Technol. 5:27–37.
90. Sanford, J. C., Smith, F. D., and Russell, J. A. 1993. Optimizing the biolistic process for different biological application. Methods Enzymol. 217:483–509.
91. Sanford, J. C., Wolf, E. D., and Allen, N. K. 1989. Biolistic apparatus for delivering substances into cells and tissues in a non-lethal manner. U.S. Pat. No. 4,945,050.
92. Sautter, C. 1993. Development of a micro-targeting device for particle bombardment of plant meristems. Plant Cell. Tiss. Org. Cult. 33:251–257.
93. Schafer, W., Gorz A., and Kahl, G. 1987. T-DNA integration and expression in a monocot crop plant after induction of Agrobacterium. Nature 327:529–531.
94. Shen, W.-H., Escudero, J., Schlappi, M., Ramos, C., John, B., and Zdena, K.-N. 1993. T-DNA transfer to maize cells: histochemical investigation of β-glucuronidase activity in maize tissues. Proc. Natl. Acad. Sci. USA 90:1488–1492.
95. Shillito, R. D., Carswell, G. K., Johnson, C. M., DiMaio, J. J., and Harms. C. T. 1989. Regeneration of fertile plants from protoplasts of elite inbred maize. Bio/Technol. 7:581–587.
96. Somers, D. A., Rines, H. W., Gu, W., Keppler, H. F., and Bushnell, W. R. 1992. Fertile transgenic oat plants. Bio/Technol. 10:1589–1594.
97. Songstad, D. D., Armstrong, C. L., and Peterson, W. L. 1991. $AgNO_3$ increases type II callus production from immature embryos of maize inbred B73 and its derivatives. Plant Cell Rpt. 9:699–702.
98. Songstad, D. D., Armstrong, C. L., Petersen, W. L., Hairston, B., and Hinchee, M. A. W. 1996. Production of transgenic maize plants and progeny by bombardment of Hi-II immature embryos. In vitro Cell Dev. Biol. 32P:179–183.
99. Songstad, D. D., Duncan, D. R., and Widholm, J. M. 1988. Effect of 1-aminocyclopropane-1-carboxylic acid, silver nitrate, and norbornadiene on plant regeneration from maize callus cultures. Plant Cell rpt. 7:262–265.
100. Southern, E. M. 1975. Detection of specific sequences among DNA fragments by gel electrophoresis. J. Mol. Biol. 98:503–517.
101. Taylor, M. G., and Vasil, I. K. 1991. Histology of, and physical factors affecting, transient GUS expression in pearl millet [*Pennisetum glaucum* (L.) R. Br.] embryos following micro-projectile bombardment. Plant Cell Rpt. 10:120–125.
102. Taylor, M. G., Vasil, V., and Vasil, I. K. 1993. Enhanced GUS expression in cereal/grass cell suspensions and immature embryos using the maize ubiquitin-based plasmid pAHC25. Plant Cell Rpt. 12:491–495.
103. Torne, J. M., Santos, M. A., and Blanco, J. L. 1984. Methods of obtaining maize totipotent tissues II. Atrophic tissue culture. Plant Sci. 40:317–325.
104. Torne, J. M., Santos, M. A., Pons, A., and Blanco, J. L. 1980. Regeneration of plants from mesocotyl tissue cultures of immature embryos of *Zea mays* L. Plant Sci. Lett. 17:339–344.
105. Uchimiya, H., Ohgawara, T., and Harada, H. 1982. Liposome-mediated transfer of plasmid DNA into plant protoplasts, p. 507–508. In: Fujiwara, A. (ed.), Proc. Fifth Annu. Intl. Cong. Plant Tiss. Cell Cult. Japan. Assoc. For Plant tissue Culture, Tokyo, Japan.
106. United States Department of Agriculture-National statistics service. 1995–96. Online internet report. Http:\\usda.mannlib.cornell. edu\usda\usda.html.
107. Vain, P., Keen, N., Murillo, J., Rathus, C., Nemes, C., and Finer, J. J. 1993. Development of the particle inflow gun. Plant Cell. Tiss. Org. Cult. 33:237–246.

108. Vasil, I. K. 1986. Developing cell and tissue culture systems for the improvement of cereal and grass crops. J. Plant Physiol. 128:193–218.
109. Vasil, V., and Vasil, I. K. 1986. Plant regeneration from friable embryogenic callus and cell suspension cultures of *Zea mays* L. J. Plant Physiol. 124:399–408.
110. Vasil, V. Lu, C.-Y., and Vasil, I. K. 1983. Proliferation and plant regeneration from the nodal region of *Zea mays* L. (Maize, Gramineae) embryos. Amer J. Bot. 70:951–954.
111. Vasil, V., Lu, C.-Y., and Vasil, I. K. 1985. Histology of somatic embryogenesis in cultured immature embryos of maize (*Zea mays* L.). Protoplasma 127:1–8.
112. Vasil, V. Srivastava, V., Castillo, A., Fromm, M. E., and Vasil, I. K. 1992. Herbicide resistant fertile transgenic wheat plants obtained by micro-projectile bombardment of regenerable embryogenic callus. Bio/Technol. 10:667–674.
113. Vasil, V., Srivastava, V., Castillo, A., Fromm, M. E., and Vasil, I. K. 1993. Rapid production of transgenic wheat plants by direct bombardment of cultured immature embryos. Bio/Technol. 11:1553–1558.
114. Walters, D. A., Vetsch, C. S., Polts, D. E., and Lundquist, C. 1992. Transformation and inheritance of a hygromycin phosphotransferase gene in maize plants. Plant Mol. Biol. 18:189–200.
115. Wang, S. A. 1987. Callus induction and plant regeneration from maize mature embryos. Plant Cell Rpt. 6:360–362.
116. Wang, Y. C. Klein, T. M., Fromm, M. E., Cao, J. Sanford, J. C., and Wu, R. 1988. Transient expression of foreign genes in rice, wheat and soybean cells following particle bombardment. Plant Mol. Biol. 11:433–439.
117. Wernicke, W., and Milkovits, L. 1986. The regeneration potential of wheat shoot meristems in the presence and absence of 2,4-dichlorophenoxyacetic acid. Protoplasma 131:131–141.
118. Xiayi, K. E., Xiuwen, Z., Heping, S., and Baojian, L. 1996. Electroporation of immature maize zygotic embryos and regeneration of transgenic plants. Transgenic Res. 5:219–221.
119. Zhong, H., Srinivasan, C., and Sticklen, M. B. 1992. In vitro morphogenesis of corn (*Zea mays* L.) I. Differentiation of multiple shoot clumps and somatic embryos from shoot tips. Planta 187:483–489.

What is claimed is:

1. A method of transforming maize tissue with exogenous DNA, comprising:
   precipitating said DNA onto tungsten microprojectiles of about 1.4–1.8 micron average size in an amount corresponding to a ratio of about 0.75–1.25 micrograms DNA per 720 micrograms of tungsten microprojectile,
   bombarding nodal explants of maize that form adventitious shoots with said DNA-bearing microprojectiles by accelerating said DNA-microprojectiles at a pressure of about 625–675 psi, said microprojectiles being expelled from a source developing said pressure upstream from said microprojectiles, wherein said nodal explants are at least 7.5 cm from said microprojectiles prior to acceleration.

2. The method of claim 1, wherein said tungsten microprojectiles prior to said precipitating step have been suspended in glycerol and frozen.

3. The method of claim 2, wherein said glycerol is a 50% solution and said microprojectiles are maintained in said frozen state for a period of at least two days prior to precipitation of DNA thereon.

4. The method of claim 1, wherein said DNA is precipitated onto said tungsten microprojectiles from a preparation comprising 2.5 M $CaCl_2$.

5. The method of claim 1, wherein said nodal explants are comprised of tissues at least 50% of which are in an active phase of cell division.

6. The method of claim 5, wherein said nodal explants are excised from germinated embryos or germinated mature seeds.

7. The method of claim 6, wherein said explants are no more than five days old.

8. A method of regenerating maize plants, comprising:
   (a) germinating maize tissue selected from the group consisting of maize embryos and maize mature seeds on a germination medium comprising MS salts, sucrose, DM-vitamins and optionally 6-benzylaminopurine, for a period of time not more than five days until germination occurs,
   (b) excising nodal section explants from said germinated maize tissue and growing said explants that form adventitious shoots on an induction medium comprising MS salts, sucrose, DM-vitamins and 6-benzylaminopurine by placing said explants on said induction medium acropetal end up until adventitious shoot formation is observed and elongating said adventitious shoots on a medium comprising sucrose, MS salts and DM-vitamins until plantlets are formed.

9. The method of claim 8, wherein said maize tissue selected is maize embryos, and said germination medium does not include 6-benzylaminopurine.

10. The method of claims 8, wherein said method of regeneration takes no more than fourteen weeks until plantlets are formed.

11. The method of claim 8, wherein said nodal section is a seventh node of said seedlings, and has a cross-section approximately 1.2–1.5 mm in length.

12. The method of claim 8, wherein said nodal explants are transformed with exogenous DNA prior to growing said explants on an induction medium.

13. The method of claim 12, wherein said exogenous DNA is introduced by bombardment of said explants with microprojectiles having said exogenous DNA precipitated thereon.

* * * * *